(12) United States Patent
Petit et al.

(10) Patent No.: US 7,651,516 B2
(45) Date of Patent: Jan. 26, 2010

(54) CONNECTION ASSEMBLY FOR THE FIELD OF SPINAL OSTEOSYNTHESIS AND METHOD FOR USING AT LEAST ONE SUCH ASSEMBLY

(75) Inventors: Dominique Petit, Verton (FR); Stephane Bette, Paris (FR); Muriel Cazin, Bussy-Saint-Georges (FR)

(73) Assignee: Spinevision S.A., Paris (FR)

( * ) Notice: Subject to any disclaimer, the term of this patent is extended or adjusted under 35 U.S.C. 154(b) by 924 days.

(21) Appl. No.: 10/282,278

(22) Filed: Oct. 28, 2002

(65) Prior Publication Data

US 2004/0092930 A1 May 13, 2004

Related U.S. Application Data

(63) Continuation-in-part of application No. 10/148,608, filed as application No. PCT/FR00/03365 on Dec. 1, 2000.

(51) Int. Cl.
*A61B 17/88* (2006.01)
(52) U.S. Cl. .................. 606/279; 606/246; 606/264; 606/265; 606/266; 606/267
(58) Field of Classification Search .............. 606/61, 606/72, 73, 246, 264–272, 274, 305–310, 606/319
See application file for complete search history.

(56) References Cited

U.S. PATENT DOCUMENTS

| | | | | |
|---|---|---|---|---|
| 5,129,900 A | * | 7/1992 | Asher et al. .......... | 606/264 |
| 5,352,226 A | * | 10/1994 | Lin .................... | 606/61 |
| 5,380,325 A | * | 1/1995 | Lahille et al. ........ | 606/61 |
| 5,527,314 A | * | 6/1996 | Brumfield et al. ..... | 606/278 |
| 5,575,791 A | * | 11/1996 | Lin .................... | 606/61 |
| 5,672,176 A | * | 9/1997 | Biedermann et al. ... | 606/271 |
| 5,741,255 A | * | 4/1998 | Krag et al. ........... | 606/264 |
| 5,947,967 A | * | 9/1999 | Barker ................. | 606/61 |
| 6,027,533 A | * | 2/2000 | Olerud ................ | 623/16.11 |
| 6,030,388 A | * | 2/2000 | Yoshimi et al. ........ | 606/61 |
| 6,086,588 A | * | 7/2000 | Ameil et al. .......... | 606/266 |
| 6,123,706 A | * | 9/2000 | Lange ................. | 606/61 |
| 6,146,383 A | * | 11/2000 | Studer et al. .......... | 606/61 |
| 6,187,005 B1 | * | 2/2001 | Brace et al. ........... | 606/61 |
| 6,248,104 B1 | * | 6/2001 | Chopin et al. ......... | 606/267 |
| 6,261,288 B1 | * | 7/2001 | Jackson ............... | 606/250 |
| 6,309,390 B1 | * | 10/2001 | Le Couedic et al. .... | 606/61 |
| 6,482,207 B1 | * | 11/2002 | Errico ................ | 606/264 |
| 6,565,569 B1 | * | 5/2003 | Assaker et al. ........ | 606/61 |
| 6,626,906 B1 | * | 9/2003 | Young ................. | 606/61 |

* cited by examiner

*Primary Examiner*—Eduardo C Robert
*Assistant Examiner*—Steven J Cotroneo
(74) *Attorney, Agent, or Firm*—Bachman & LaPointe, P.C.

(57) ABSTRACT

A connection assembly for spinal osteosynthesis has a bone-anchor having a connection zone intended to cooperate with a connection device, in which the connection device has, in its lower part, a spherical shape in order to permit a free positioning of the connection device in connector. The connector has a cavity of complementary shape to the spherical shape. This spherical shape forms a limit of longitudinal positioning with the connector.

15 Claims, 24 Drawing Sheets

CONNECTION ASSEMBLY FOR THE FIELD OF SPINAL OSTEOSYNTHESIS AND METHOD FOR USING AT LEAST ONE SUCH ASSEMBLY

CROSS-REFERENCE TO RELATED APPLICATION

This application is a Continuation-In-Part of pending U.S. patent application Ser. No. 10/148,608, filed Sep. 3, 2002, which is a National Stage filing of PCT/FR00/03365, filed on Dec. 1, 2000.

BACKGROUND OF THE INVENTION

The subject of the present invention concerns an application in the field of spinal osteosynthesis.

The present invention relates more particularly to a connection assembly for spinal osteosynthesis comprising a bone-anchoring means having a connection zone intended to cooperate with a connection means, and also to a method for using at least one such assembly.

Connection assemblies are known in the prior art, in particular German utility model No. 92 15 561.

The major disadvantage of the connection assemblies in the prior art lies in the fact that they afford only slight possibility of movement of the various elements relative to one another.

More precisely, the connection assemblies in the prior art afford only a reduced amount of freedom of movement of the various elements.

SUMMARY OF THE INVENTION

An important aim of the present invention is to make available a connection assembly affording a greater amount of freedom of movement of the various elements relative to one another.

The present invention thus permits, before final implantation of said connection assembly, that the linking element is free in rotation relative to the anchoring means in three axes of rotation and is free in translation relative to the anchoring means in two directions of translation.

The present invention concerns in its most general sense a connection assembly as claimed in claim 1.

The connection assembly according to the invention is characterized in that the connection means has, in its lower part, a spherical shape in order to permit a free positioning of the connection means in a connector, said connector having a cavity of complementary shape to said spherical shape, this spherical shape forming a limit of longitudinal positioning with the connector.

The connection means is advantageously crimped in the connector in such a way as to join the two components while allowing a rotation of the connection means in the connector.

According to one variant, the connector has a cone of admission into the connector for the passage of the ancillary device for driving the connection means in rotation.

The angular clearance of the connector on the connection means is preferably about 30 degrees when the ancillary device for driving the connection means in rotation is in place.

According to a preferred embodiment, the connection means has slots machined in the spherical part of the connection means in such a way as to create a deformation upon final tightening of the system. Said slots are preferably longitudinal.

Said connection means preferably comprises, also in its lower part, a skirt. This skirt is threaded on its lower end to facilitate its penetration into the bone.

Said bone-anchoring means preferably comprises, in its upper part, a part for preliminary guiding of said connection means in order to permit good alignment of the connection means with the screw.

The connection means can be formed by a nut.

The connector is provided with at least one site for receiving a linking element.

The connector can comprise a blocking site opening out into the cavity forming the seat of the spherical shape and into the site receiving the linking element.

In one variant, the connection assembly according to the invention can comprise a blocking nut which can be introduced into said blocking site.

In another variant, the connection assembly according to the invention can comprise a blocking cylinder which can be introduced into said blocking site. This blocking cylinder can be replaced by a linking element.

The blocking site can additionally open out also in a substantially perpendicular direction for the introduction of a blocking nut. The blocking nut can comprise a stud intended to cooperate with a site formed in said blocking cylinder.

The site for receiving a linking element can be of oblong shape in the case of a connector of the closed type, or of a "U" shape opening out on one of the faces in the case of a connector of the open type.

The connector can be provided with two sites for receiving a linking element formed by an angled rod forming a U closed at its ends and the linking element has a cavity of complementary shape to the spherical shape.

A threaded part, of hexagon shape, is preferably formed at the upper end of the connection means in order to allow a secondary nut to be screwed on.

The present invention also relates to a method for using at least one connection assembly for spinal osteosynthesis, in which at least one linking element is connected to a bone-anchoring means with the aid of said connection assembly, said bone-anchoring means comprising a connection zone intended to cooperate with a connection means, and the connection means having, in its lower part, a spherical shape in order to permit a free positioning of the connection means in a connector having a cavity of complementary shape to said spherical shape, this spherical shape forming a limit of longitudinal positioning with the connector.

In this method, the connection means ensures the fixation of said bone-anchoring means relative to the connector.

According to a first variant of the implantation method, the connection means is first pre-fitted in said connector, the bone-anchoring means is then placed in the bone, and the connection means is then introduced along the anchoring means.

In this first variant, the linking element is engaged in the connector before or after the introduction of the connector on the anchoring means.

According to a second variant of the implantation method, and in succession, the bone-anchoring means is first placed in the bone, the connector, equipped with the linking element, is then introduced along the anchoring means, and the connection means is finally introduced along the anchoring means.

According to a third variant of the implantation method, before implantation in the bone, the connection assembly according to the invention is pre-fitted without the anchoring means, and the anchoring means is then introduced into the bone via said connection means, when the connection assembly is correctly positioned against the bone.

In this method also, the bone-anchoring means can be removed after implantation of said connector without modification of the positioning of said connector, either to be changed or to be repositioned.

BRIEF DESCRIPTION OF THE DRAWINGS

The present invention will be better understood on reading the following description of a nonlimiting illustrative embodiment, reference being made to the attached figures, in which:

FIG. 15 shows a perspective view of the implantation of two bone-anchoring means in a portion of the spine;

FIG. 16 shows a perspective view of the implantation of three connectors and of a linking rod in the portion of the spine from FIG. 15;

FIG. 17 shows a perspective view of the positioning of the three connectors from FIG. 16 against the portion of the spine by screwing of a first bone-anchoring means;

FIG. 18 shows a perspective view of the implantation of a third bone-anchoring means in the portion of the spine from FIG. 17;

FIG. 19 shows a perspective view of the osteosynthesis system from FIG. 18 when the third anchoring means is screwed completely in the corresponding connector;

FIG. 20 shows a perspective view of the osteosynthesis system from FIG. 19 when the connection means of the second connector is introduced on the second anchoring means;

FIG. 21 shows a perspective view of the osteosynthesis system from FIG. 20 when the connection means of the second connector is fixed on the corresponding connector;

FIG. 22 shows a perspective view of the osteosynthesis system from FIG. 21 when the anchoring means of the second connector is screwed on the corresponding connector;

FIG. 23 shows a perspective view of the osteosynthesis system from FIG. 22 when the anchoring means of the first connection assembly is unscrewed from the corresponding connector;

FIG. 24 shows a perspective view of the osteosynthesis system from FIG. 23 when the anchoring means of the first connection assembly is re-screwed in the corresponding connector, but in a different orientation; and FIG. 25 shows a front view of the osteosynthesis system from FIG. 24.

DETAILED DESCRIPTION OF THE PREFERRED EMBODIMENTS

Figure 1:
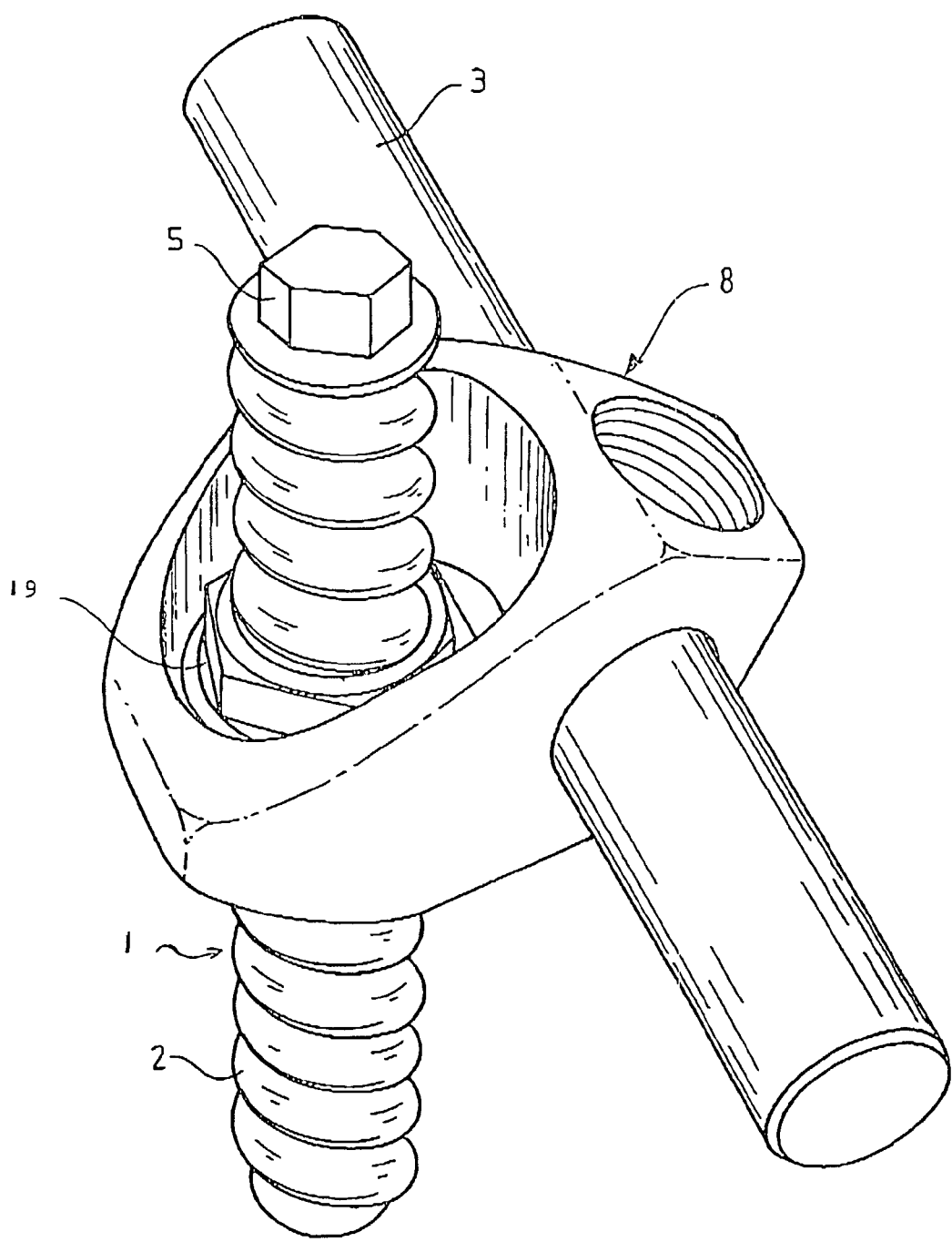
FIG. 1 shows a perspective view of a connection assembly in its basic version with a bone-anchoring means screw.

The present invention relates to a connection assembly, illustrated in its basic version in FIG. 1, for spinal osteosynthesis, comprising a bone-anchoring means having a connection zone (29) intended to cooperate with a connection means.

The bone-anchoring means can be formed by a screw (1) having at least one bone thread (2).

The screw (1) additionally comprises a connection zone (29) intended to cooperate with said connection means.

The bone-type thread (2) has a principal function: namely that of ensuring anchoring in the bone. It may possibly have a secondary function: namely that of receiving the connection system for a linking element when the connection zone (29) merges with the upper part of the bone thread (2).

A system for driving in rotation (5) is provided on the upper end of the screw (1). This system, for example a hexagon, has two functions: that of enabling the screw (1) to be driven in rotation upon penetration of the latter into the bone, but also a role of blocking in terms of rotation during the final tightening of the mechanism in order to avoid further penetration of the screw (1) into the bone.

The connection means permits formation of a longitudinal limit stop along the screw (1) by way of a connector (8).

The connection means can be formed by a nut (19). In this case, the internal threading (7) of the nut (19) corresponds to the thread of the connection zone (29); that is to say, in the version illustrated in FIGS. 1, 2 and 3, to the bone thread (2) of the screw (1). The nut (19) is screwed on the part of the screw not engaged by the bone.

The nut (19) is of spherical shape (20) in its lower part. This spherical shape is intended to permit a free positioning of the nut (19) on the connector (8) where a seat of the same type is provided. This spherical shape (20) also serves as a limit of longitudinal positioning with the connector (8). In the preferred application, the connection means is crimped in the connector (8)in such a way as to join the two components while allowing a rotation of the connection means on the connector (8)

Figure 3:
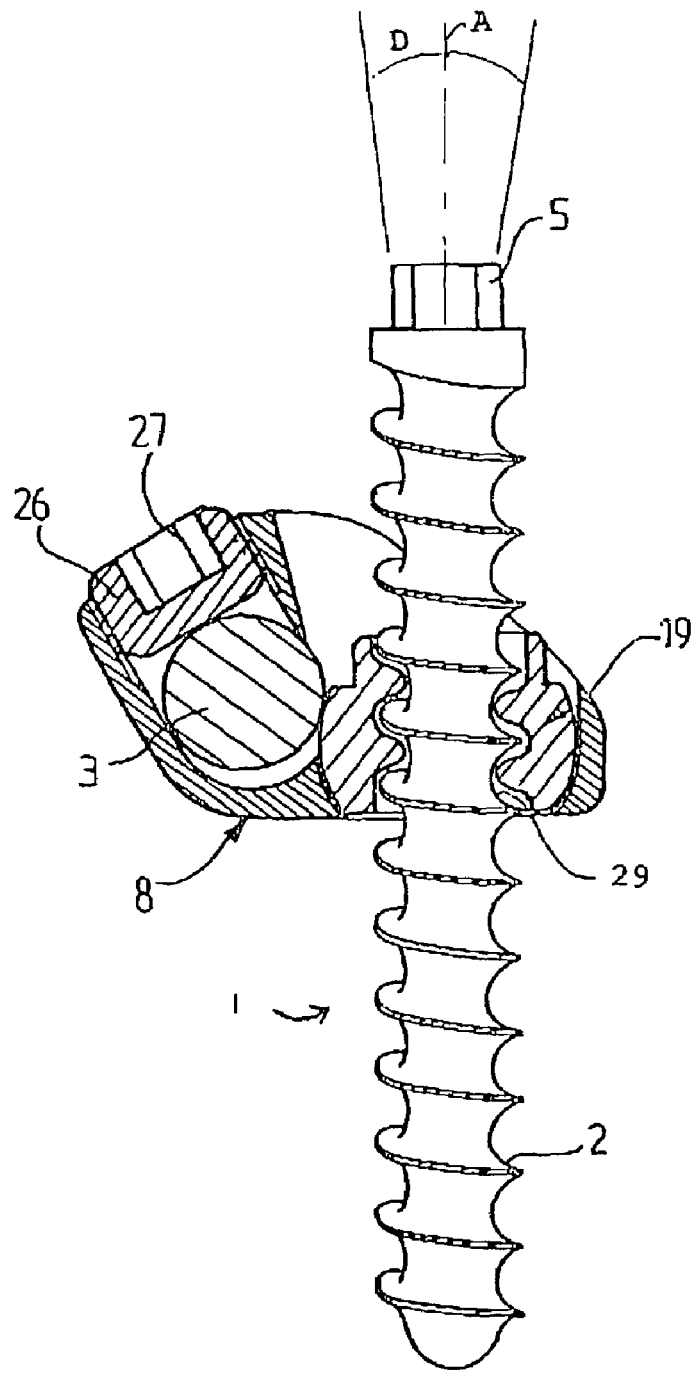
FIG. 3 shows a partial cross-sectional view of the connection assembly in FIG. 1.

A drive system (21), for example an external hexagon, is also provided on the connection means above its spherical part (20) in such a way as to permit adjustment of its height and that of the connector (8) along the screw (1). As a consequence of the possibility of rotation of the connector on the connection means, a cone (22) of admission into the connector (8) is provided for the passage of the ancillary device for driving the connection means in rotation. By way of example, in the preferred application the angular clearance D of the axis A of the connector on the connection means is 30 degrees when the ancillary device for driving the connection means in rotation is in place, as is illustrated in FIG. 3.

Slots (23) are machined in the spherical part of the connection means in order to create a deformation upon final tightening of the system. The purpose of this deformation is to block the screw (1) in rotation.

Figure 2:
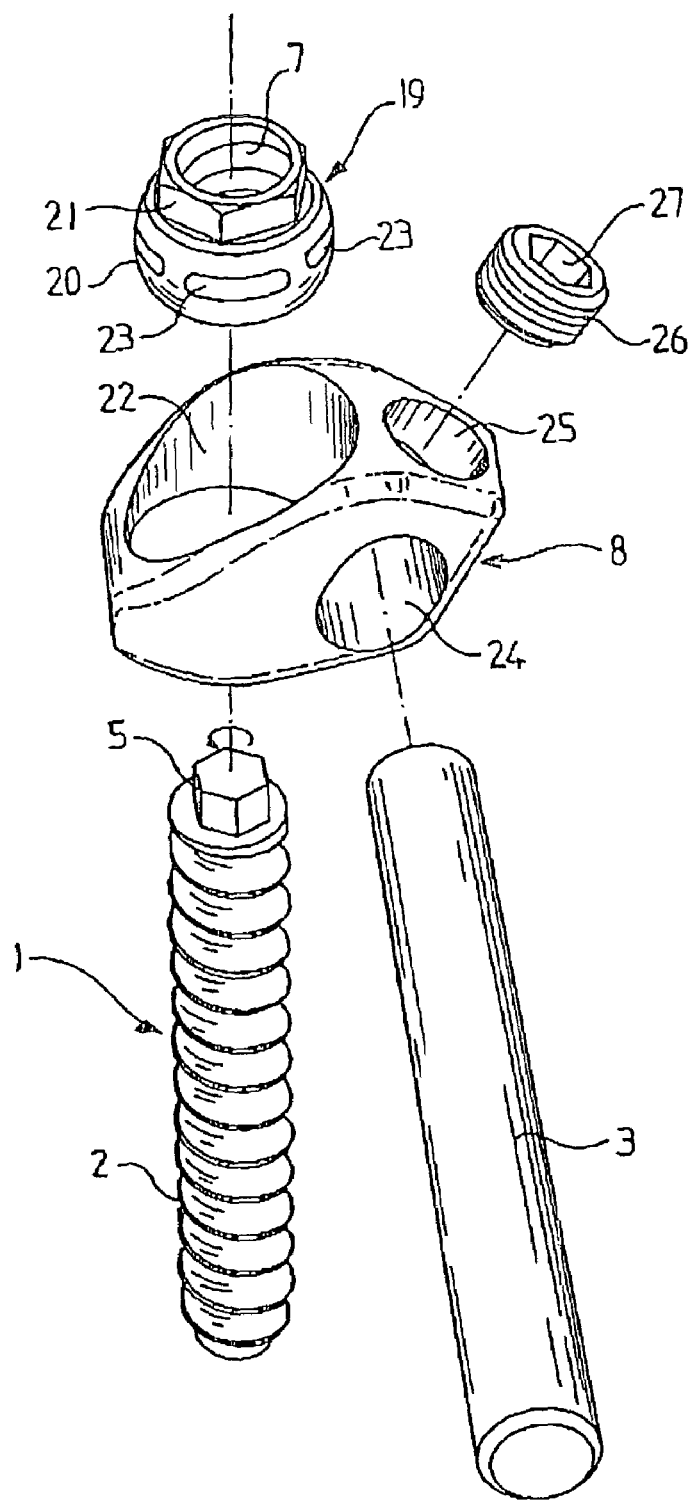
FIG. 2 shows an exploded view of the connection assembly in FIG. 1.
Figure 4:
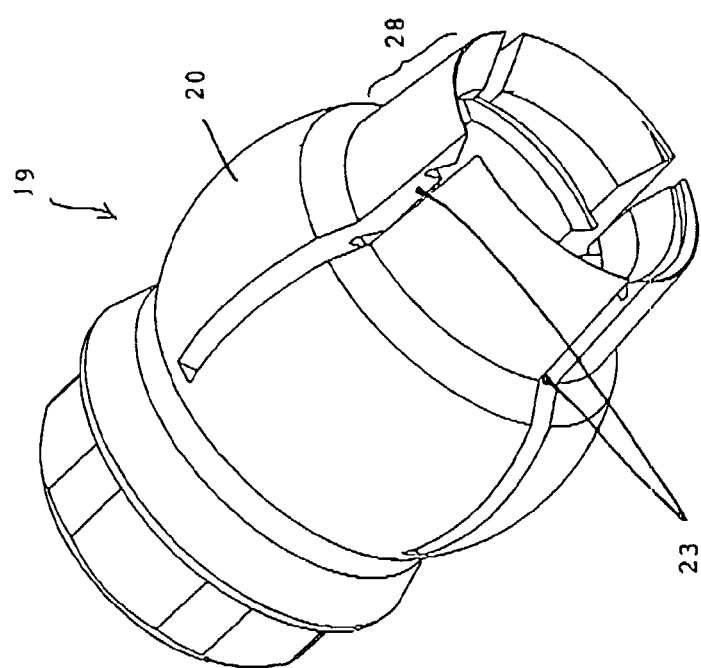
FIG. 4 shows a perspective view of a nut according to the invention with skirt and longitudinal slots.

The slots (23) can be positioned transversely, as is illustrated in FIG. 2, or longitudinally, as is illustrated in FIG. 4.

The longitudinal slots preferably open out in the lower part of the spherical shape (20). There can be one, two, three, four, five or more of them.

Figure 5:
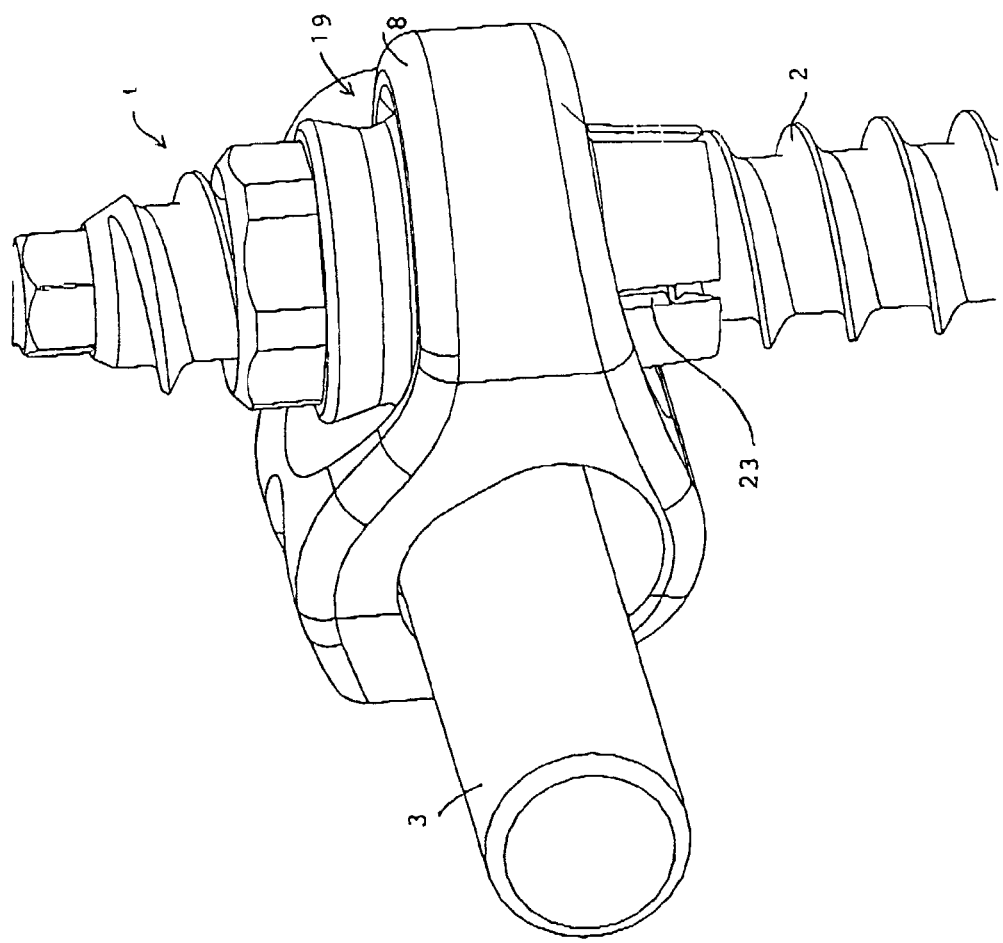
FIG. 5 shows a partial perspective view of a nut according to FIG. 4 mounted on a connector.

In its lower part, the connection means has a skirt, which can also be seen in FIG. 4, and in FIG. 5. This skirt (28) permits a mechanical transition between the screw (1) and the spherical shape (20). This is because too abrupt a transition would promote rupturing of the screw at the base of the spherical shape (20) under dynamic forces. The skirt (28) thus makes it possible to better distribute the stress of engagement of the screw in the nut.

This skirt (28) can be threaded on its end in order to facilitate its penetration into the bone.

Figure 6:
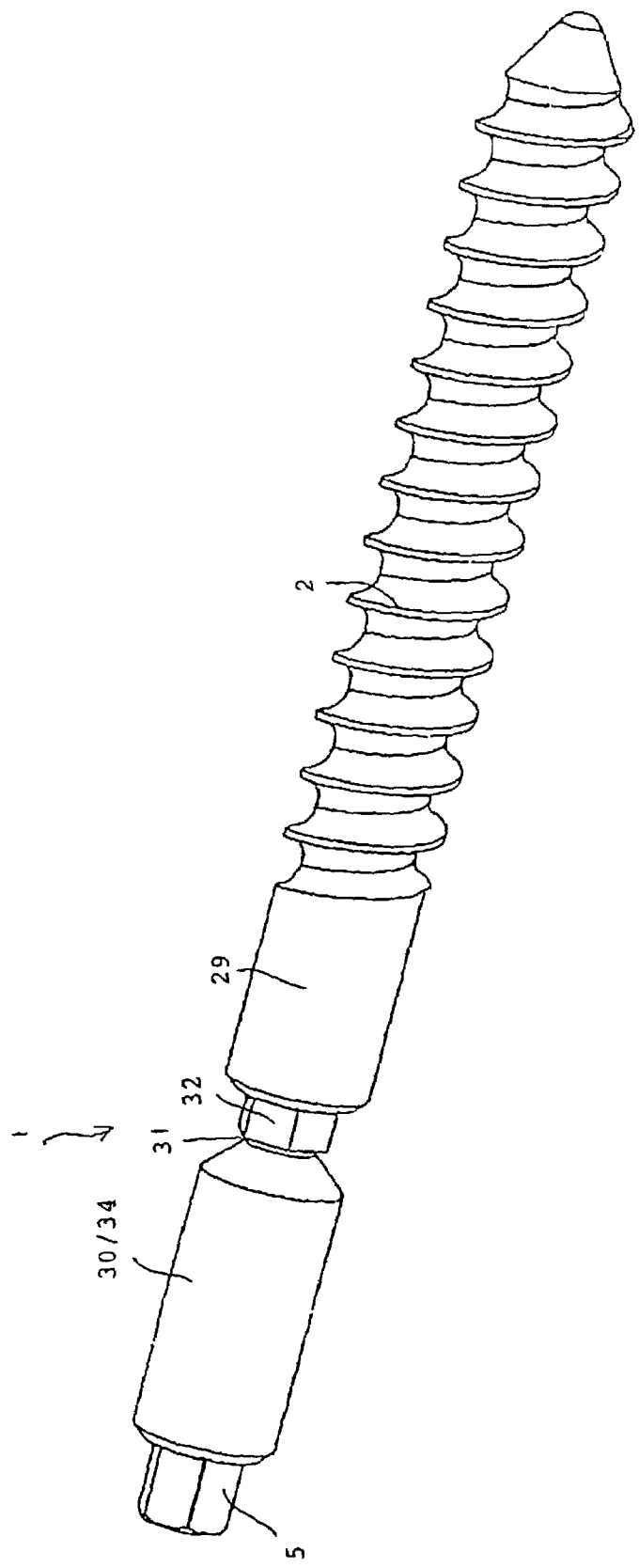
FIG. 6 shows a perspective view of a screw having a smooth preliminary guiding part and/or return part, and also a smooth connection part.
Figure 7:
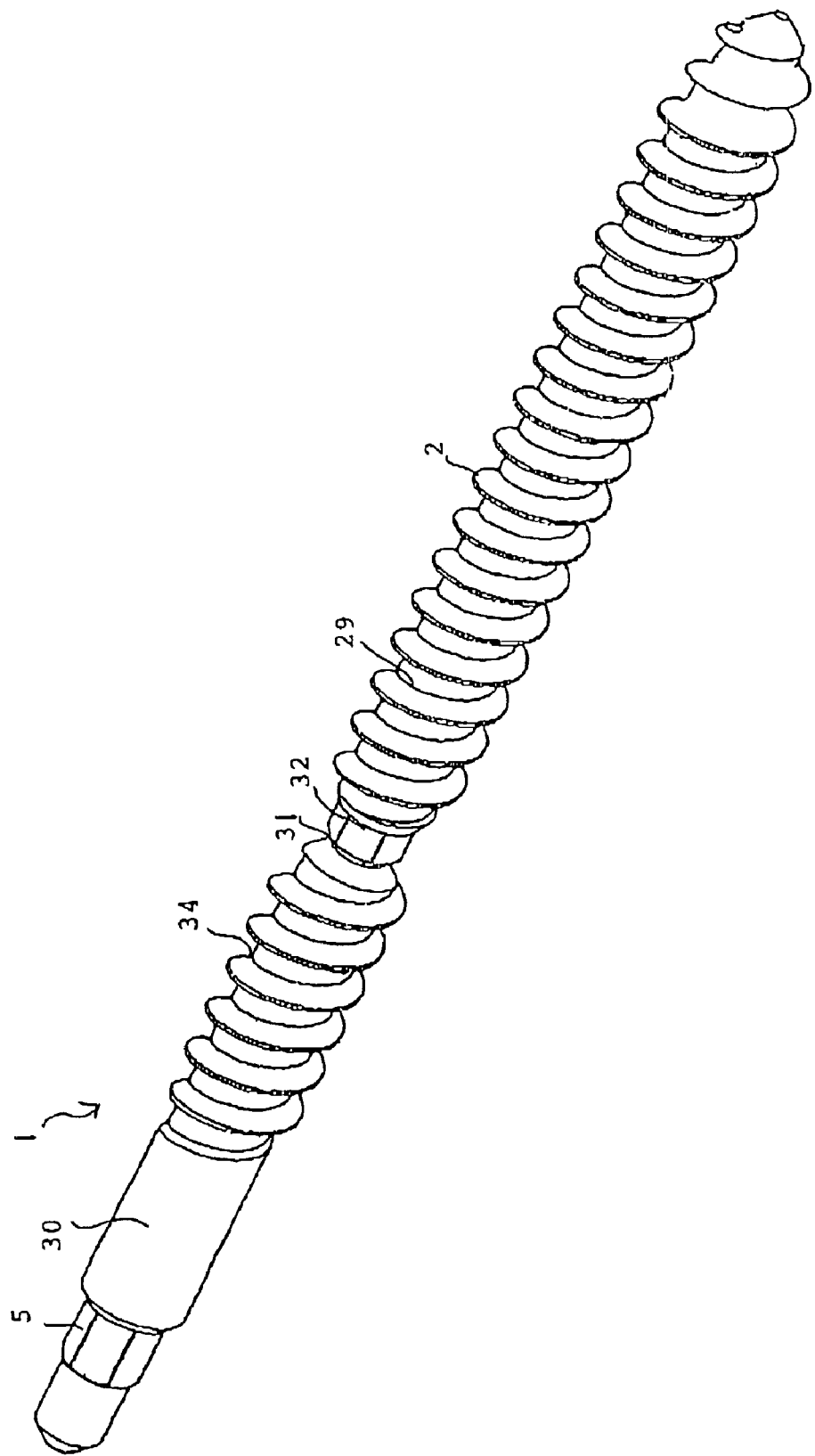
FIG. 7 shows a perspective view of a screw having a smooth preliminary guiding part, a threaded return part, and a threaded connection part merging with the bone thread.
Figure 8:
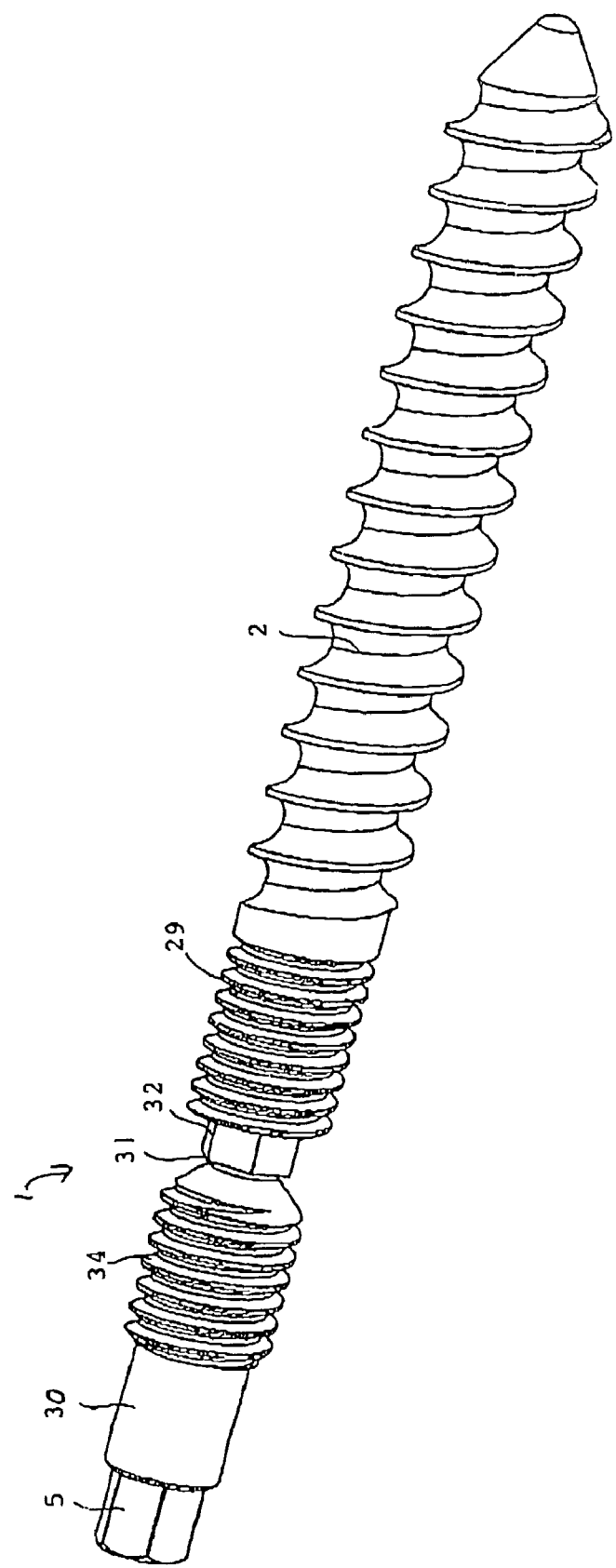
FIG. 8 shows a perspective view of a screw having a smooth preliminary guiding part, a threaded return part, and a threaded connection part not merging with the bone thread.
Figure 9:
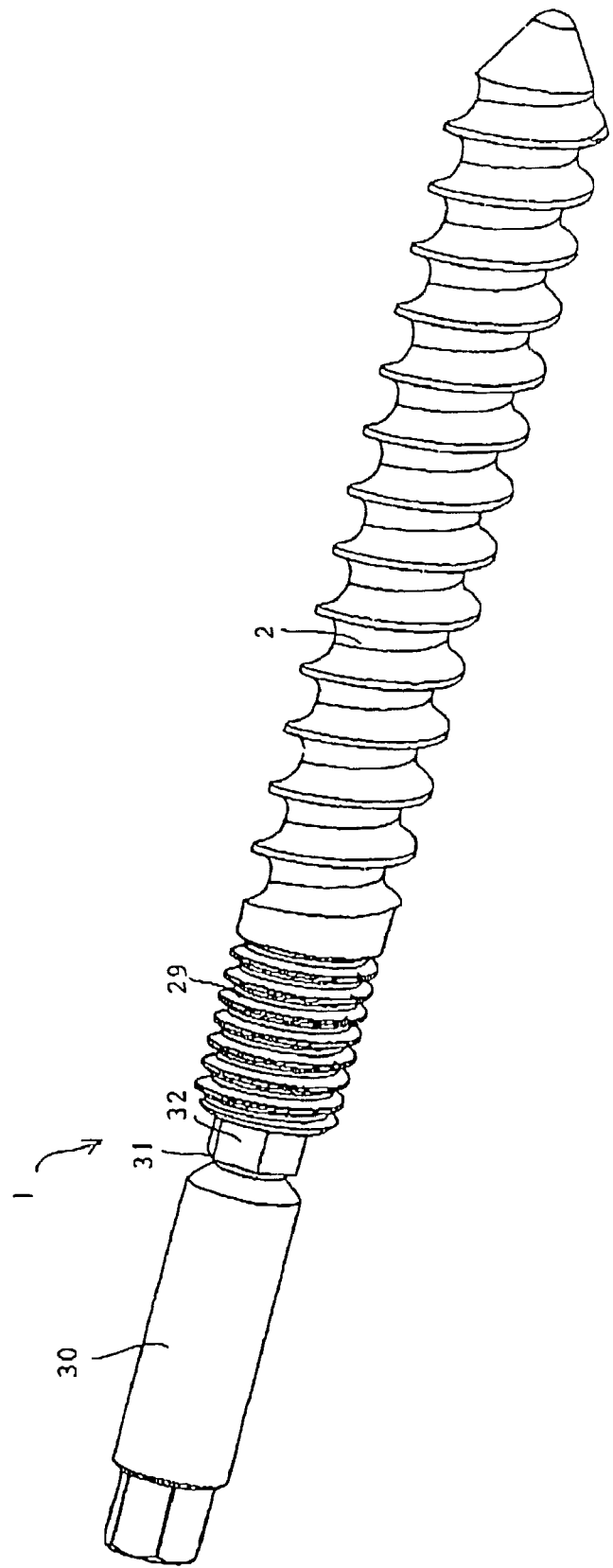
FIG. 9 shows a perspective view of a screw having a smooth preliminary guiding part, and a threaded connection part not merging with the bone thread.

The connection zone (29) of the screw (1) can be formed in the upper part of the bone thread and can have a thread identical to the bone thread, as is illustrated in FIG. 7, but it can also have a different thread, as is illustrated in FIGS. 8 and 9, or can be unthreaded, as is illustrated in FIG. 6.

In the latter case, the connection means consequently has a smooth inner wall and does not constitute a nut.

In one variant, the screw (1) has, in its upper part, a smooth preliminary guiding part (30) in order to ensure good alignment of the connection means when the connection means is put into place, a fortiori when it is a nut (19).

This preliminary guiding part (30) has a smooth wall, as is illustrated in FIGS. 6 through 9. Its external diameter is substantially equivalent to that of the internal diameter of the connection means in order to ensure longitudinal guiding which is as linear as possible (without angular incline).

The smooth preliminary guiding part (30) can also serve as a return zone (34) in the case of treatment of spondylolisthesis.

This return zone (34) can also be threaded with a thread identical to the bone thread (2), as is illustrated in FIG. 7, or with a different thread, as is illustrated in FIG. 8.

The screw (1) can also be provided with a slot (31) facilitating the detachment of the top of the screw (1) comprising the smooth preliminary guiding part (30) and/or the return zone (34). Under this circular slot (31), a drive system (32) is machined which, after rupture, becomes the drive system of the screw (1), particularly for the removal of the connection assembly, as is illustrated in FIGS. 7 through 9.

In the basic version, the connector (8) is provided with a single site for receiving a linking element (3) formed by a rod. This site can be of oblong shape (24) in the case of a connector (8) of the closed type, or can be of a "U" shape opening out on one of the faces in the case of a connector of the open type. In the case of a connector (8) of the closed type, the rod must be engaged into the latter, while in the case of an open connector the rod (3) can be introduced onto the connector posteriorly or laterally.

The site (24) for receiving the rod (3) is provided in such a way that the rod (3) can bear on the spherical shape (20) of the nut (19), as is illustrated in FIG. 3.

It will thus be appreciated that the rod (3), relative to the screw (1), is free in three axes of rotation and in two directions of translation:

Rotation of the connector (8) and thus of the rod (3) about the connection means in two axes perpendicular to the screw (1);

Rotation of the connector (8) and thus of the rod (3) about the connection means in an axis identical to that of the screw (1);

Translation of the rod (3) in the connector (8) along the axis thereof;

Translation of the connector (8) and thus of the rod (3) along the screw (1) by virtue of the possibility of regulating the connection means.

In addition, the rotation of the rod (3) about itself can afford a supplementary degree of freedom for the connection assembly.

The connector (8) also has a blocking site (25) for receiving a blocking system. In the basic application, this blocking system is a nut (26) provided with a drive system (27) for applying a torque sufficient to ensure good mechanical stability of the assembly, as is illustrated in FIG. 3.

The blocking of such a connection is ensured by the pressure of the linking element (3) on the spherical shape (20). As the linking element (3) is secured on the connector (8) by the pressure exerted by the nut (26), the degrees of freedom are thus all fixed.

Figure 10:
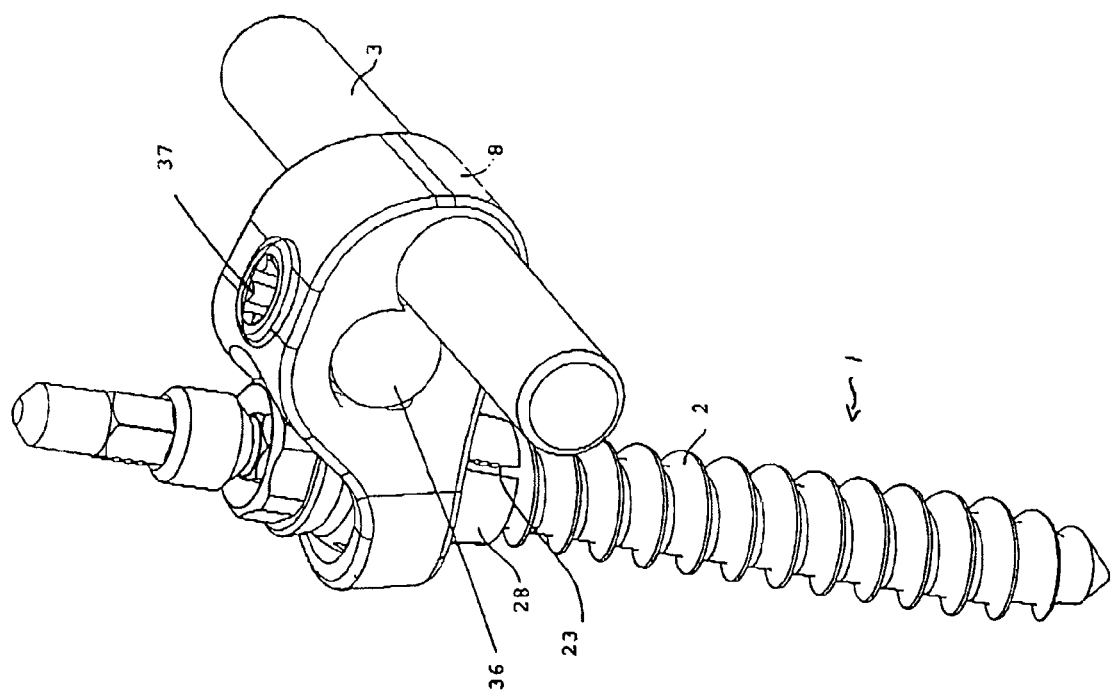
FIG. 10 shows a perspective view of a connection assembly with a blocking system between the connection means and the connection rod.

In one variant, said connector (8) has a more advanced blocking site (25) in which a blocking cylinder (36) can be introduced, said blocking site (25) also opening out in a substantially perpendicular direction for the introduction of a blocking nut (37), as is illustrated in FIG. 10.

Figure 11:
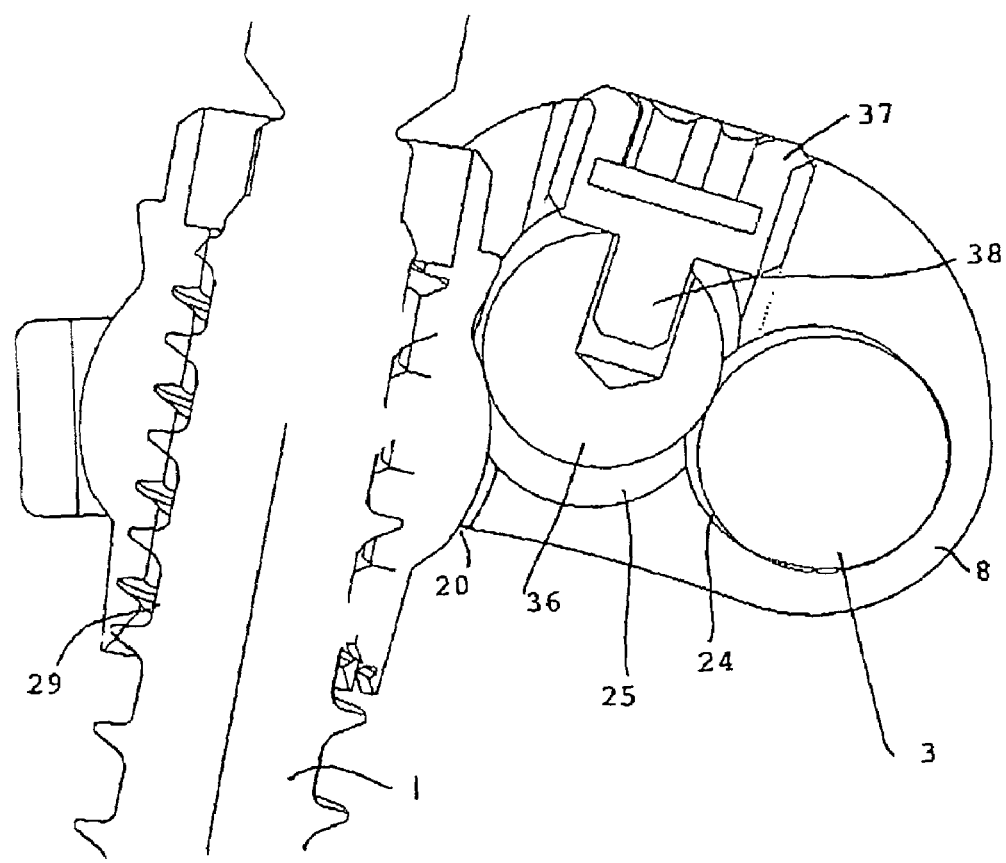
FIG. 11 shows a cross-sectional view of the connection assembly from FIG. 10 with a blocking cylinder.

In addition, said blocking nut (37) has a stud (38) intended to cooperate with a site formed in said blocking cylinder (36) in order to ensure that the blocking cylinder (36) does not detach from the connector when the assembly is not yet tightened, as is illustrated in FIG. 11.

Figure 12:
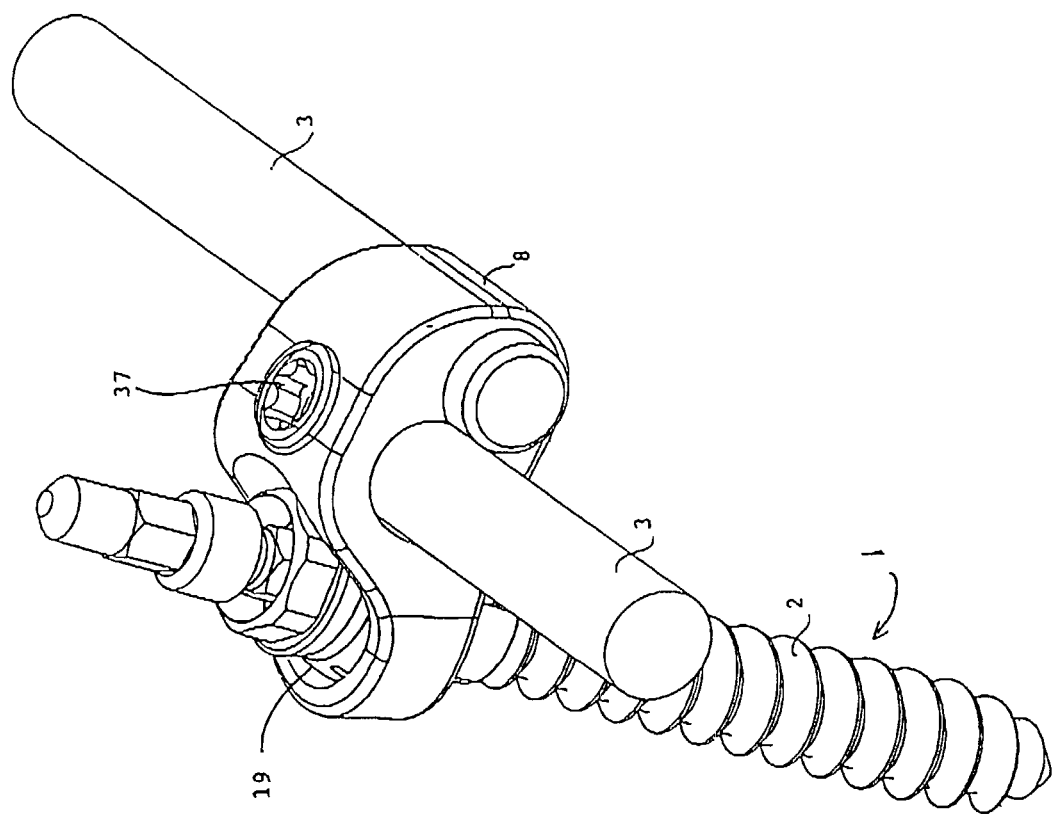
FIG. 12 shows a perspective view of the connection assembly from FIG. 10 with a second connection element.

The blocking cylinder (36) can be replaced by a second linking element (3) in order to afford an additional possibility of connection, as is illustrated in FIG. 12.

In this version, the tightening of the assembly is ensured by the force which is exerted both on the linking element (3) and on the spherical part (20) by the connection cylinder (36) or by the second linking element (3).

It is necessary to provide a plurality of connectors so as to be able to choose one in which the distance between the screw and the linking element or linking elements is suitable.

Figure 13:
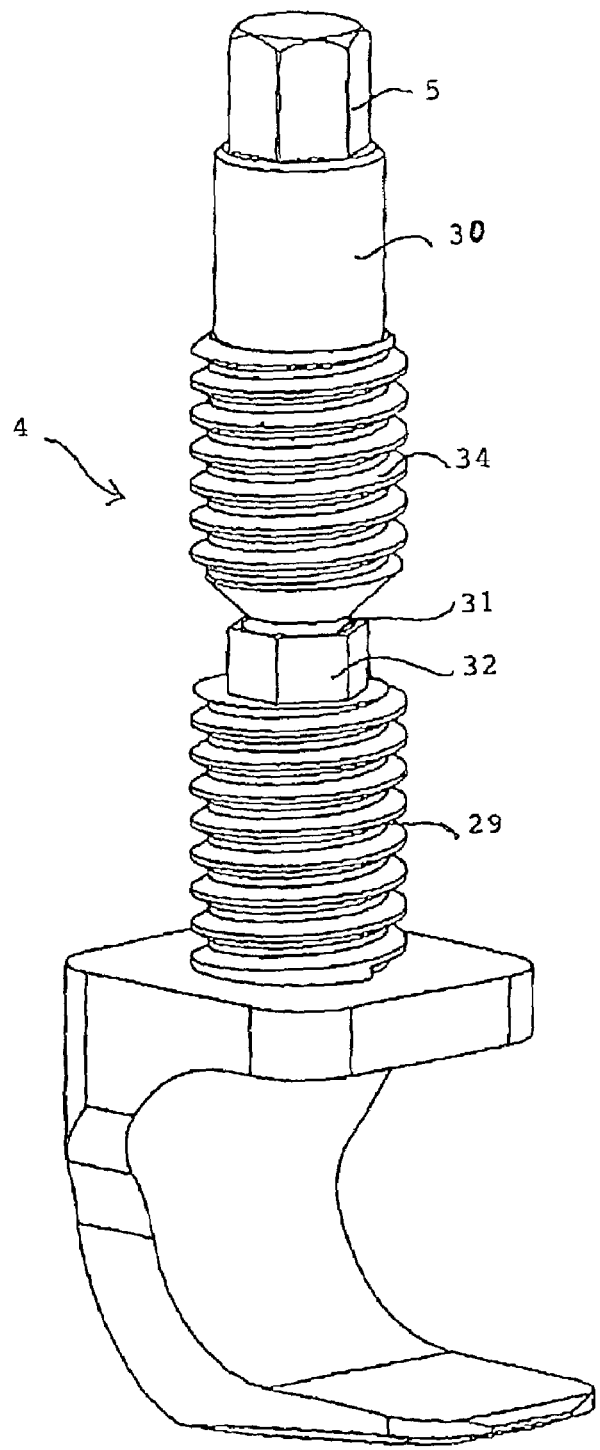
FIG. 13 shows a perspective view of; a hook-type anchoring means.
Figure 14:
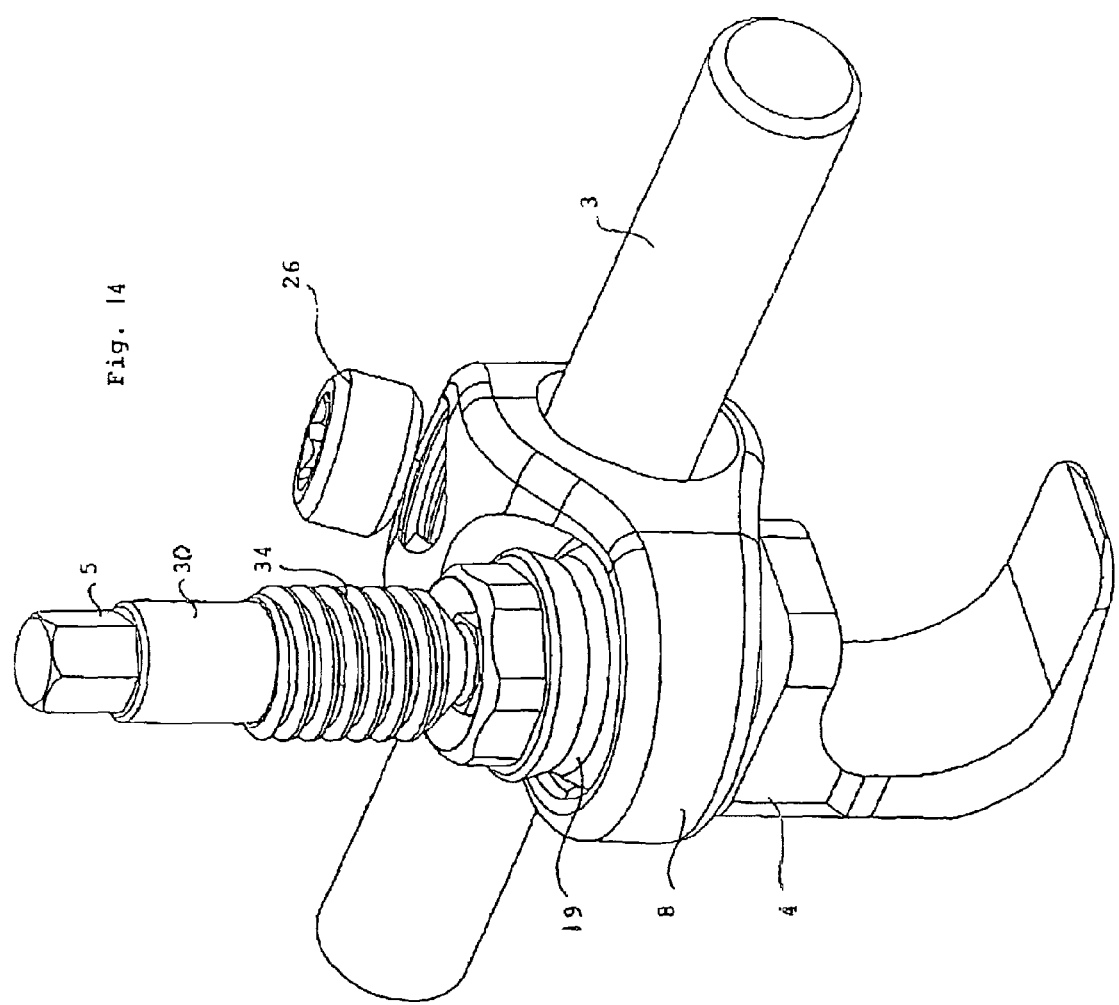
FIG. 14 shows a perspective view of a connection assembly with a hook-type anchoring means.

The bone-anchoring means can also be formed by a hook (4), as is illustrated in FIGS. 13 and 14.

When using at least one connection assembly for spinal osteosynthesis according to the invention, the connection means ensures the fixation of said bone-anchoring means relative to the connector (8).

In a first variant of implantation of a connection assembly according to the invention, the bone-anchoring means (1) is first placed in the bone. The connector (8) pre-fitted with the connection means already crimped in the cavity is then introduced along the anchoring means. In this first variant, the linking element (3) can be engaged in the connector before or after introduction on the anchoring means.

In a second variant of implantation of a connection assembly according to the invention, the bone-anchoring means (1) is first placed in the bone. The connector (8), equipped with the linking element (3), is then introduced, via the spherical cavity of the connector, along the anchoring means (1), but at this stage the connection means is not yet positioned in the cavity of the connector (8) intended to receive it. The connector (8) slides without any difficulty along the anchoring means (1) because the opening of the spherical cavity is greater than the external diameter of the bone-anchoring means.

Then, once the connector is substantially positioned against the bone, the connection means is introduced along the anchoring means. On arriving in the spherical cavity, the connection means provokes the lateral displacement of the linking element in the oblong site (24) of the connector (8) in order to allow the connection means to pass under the linking element.

By driving the drive system (21) of the connection means, the connection means is thus crimped in the spherical cavity. The positioning of the connection element and its crimping are thus performed in situ. The nut (26) can then be screwed in order to definitively fix the connection assembly and the linking element.

In a third variant of implantation of a connection assembly according to the invention, before implantation in the bone, the connection assembly according to the invention is pre-fitted, without the anchoring means, that is to say the linking element (3) is positioned in the oblong site (24) of the connector (8) and the connection means is crimped in the spherical cavity of the connector (8). It is thus easy to exactly position the linking element at the desired site. This is particularly intended for fixation of a linking element with the aid of at least three connection assemblies; this is because, in this situation, it is of course always difficult to succeed in positioning the at least three connection assemblies without the linking element being subjected to considerable forces of alignment.

In this third variant, the anchoring means is introduced into the bone via said connection means, by virtue of the internal threading (7), only when the connection assembly is correctly positioned against the bone. The hole intended to receive the anchoring means may or may not be prepared in advance. In the case where the hole is prepared in advance, it is possible to introduce pins into it for supporting the connection assembly and for more precise positioning of the connection assembly with the linking element. In the case where the hole is not prepared in advance, it is possible to make it via the connection means with a suitable ancillary device or to use a self-tapping anchoring means.

Upon positioning of the connection means, its alignment relative to the axis of the cavity formed for receiving the spherical shape (20), and in particular relative to the axis of the cone of admission (22) of the connector (8), can be ensured by the preliminary guiding part (30) situated on the bone-anchoring means.

The orientation of the connection means is chosen as a function of the desired orientation of the bone-anchoring means. Thus, by virtue of the large degree of freedom of the connection means relative to the connector (8), it is also possible to orient the anchoring means with a large degree of freedom.

The blocking of the linking element relative to said connector (8) is ensured:
  either by screwing a blocking nut (26) into a site (24) receiving the linking element (3),
  or by introducing a blocking cylinder (36) into a blocking site (25) which opens out on the one hand into the cavity forming the seat of the spherical shape (20) and on the other hand into a site (24) receiving the linking element (3), and by blocking said blocking cylinder (36) with the aid of a blocking nut (37).
  or by introducing a second linking element (3) into a blocking site (25) which opens out on the one hand into the cavity forming the seat of the spherical shape (20) and on the other hand into a site (24) receiving a first linking element (3), and by blocking said second linking element (3) with the aid of a blocking nut (37).

Upon final tightening of said connection assembly, the longitudinal or transverse slots (23) machined in the spherical part (20) of the connection means deform.

In a particularly advantageous manner, the slot (31), preferably formed on the anchoring means, is such that the force exerted to generate rupturing of the bone-anchoring means at the level of this rupture slot (31) by means of rotation corresponds to the force required to ensure the final tightening of said connection assembly. Thus, if the anchoring means (1) does not break but instead turns inside the connector (8), this means that the blocking nut (26 or 37) is not sufficiently tightened.

In a likewise particularly advantageous manner, the bone-anchoring means can be removed after implantation of said connector without modification of the positioning of said connector (8).

Thus, it is possible to change the anchoring screw, for example in order to replace it with a screw which has the same diameter and same thread but is shorter or longer, without dismantling the connector (8), during the implantation of the connection assembly or after the implantation of this assembly, or else to modify the orientation of the screw relative to the connector in order to permit a better quality of bone anchoring.

The method according to the invention can also be used to fit a patient with several connection assemblies for spinal osteosynthesis according to the invention.

These connection assemblies can in fact be used to implant all or part of an osteosynthesis system in a patient during a single operation or in several operations.

Each connection assembly according to the invention used in the osteosynthesis system can be put in place in accordance with one of the three variants above.

FIGS. 15 through 25 illustrate these three variants of implantation of the connection assembly according to the invention for the positioning of an osteosynthesis system.

In these figures, the three adjacent vertebrae in which connection assemblies are implanted in accordance with the three variants are indicated as 100, 200 and 300, respectively. The vertebra (100) has undergone implantation according to the first variant, the vertebra (200) has undergone implantation according to the second variant, and the vertebra (300) has undergone implantation according to the third variant, in order to explain in detail each of these variants. In practice, there is of course no obligation to use the three different variants for three adjacent vertebrae; it is for the surgeon to choose between the different variants for each vertebra.

Figure 15:
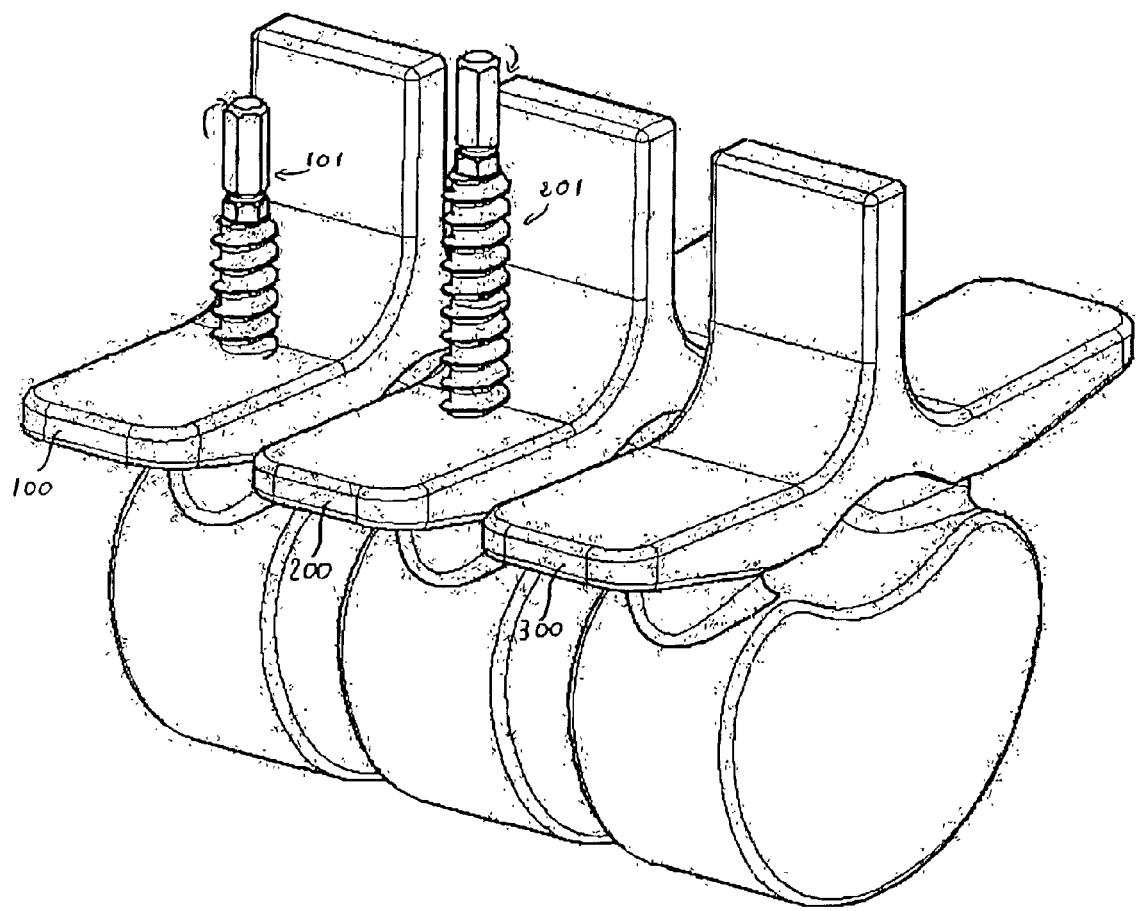
FIGS. 15 through 25 illustrate the different variants of implantation of the connection assembly according to the invention for positioning of an osteosynthesis system.

FIG. 15 illustrates the implantation of two anchoring means (101, 201), formed by screws, in the vertebrae (100, 200) respectively.

Figure 16:
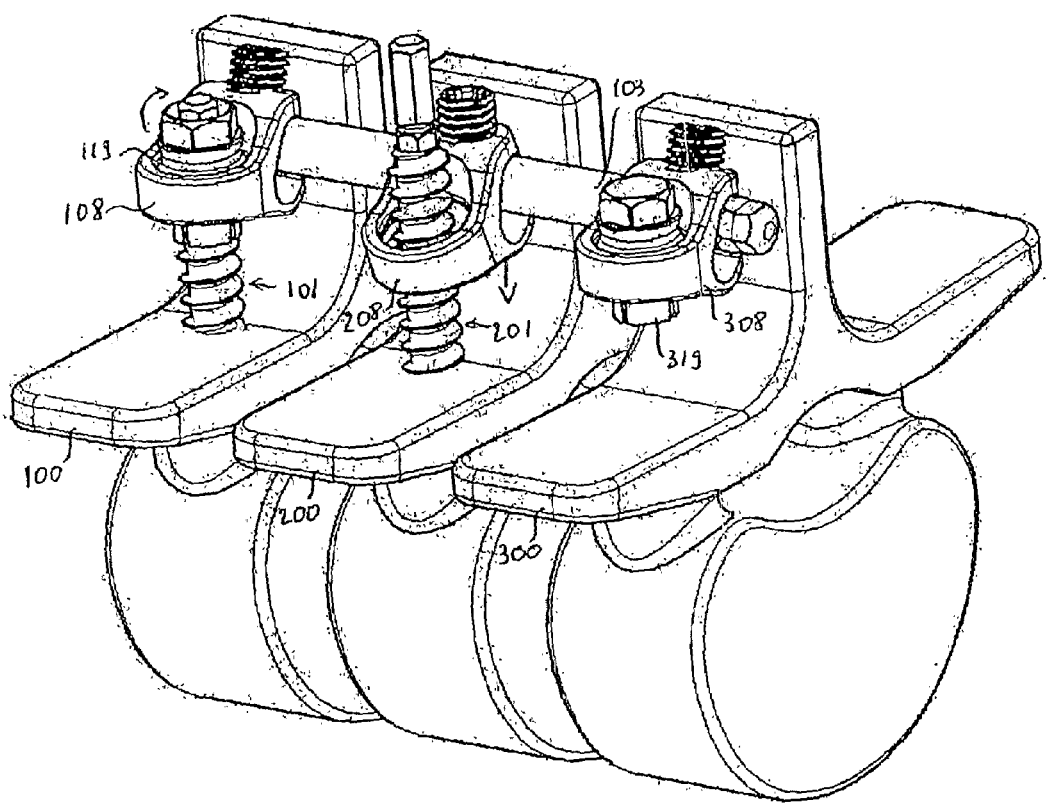

FIG. 16 illustrates the positioning of a connector (108) along the anchoring means (101), the connector (108) being pre-fitted with a connection means formed by a nut (119) already crimped in the cavity and with the linking element (103) engaged on the connector, in accordance with the first variant of implantation.

FIG. 16 also illustrates the positioning of a connector (208) without connection means, engaged on the linking element (103) and along the anchoring means (201), in accordance with the second variant of implantation.

FIG. 16 also illustrates the positioning of a connector (308) without anchoring means, but with a connection means formed by a nut (319), said connector (308) being engaged on the linking element (103), in accordance with the third variant of implantation.

Figure 17:
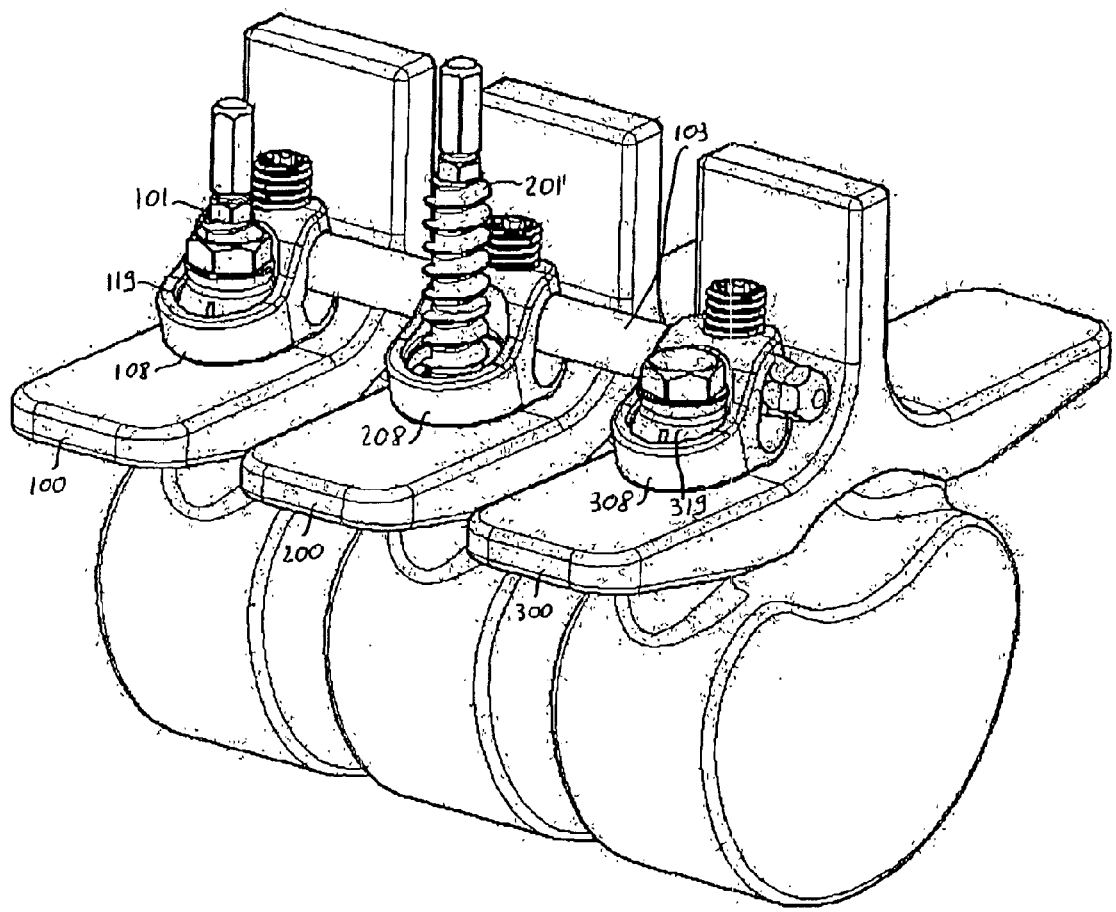

FIG. 17 illustrates the positioning of the connector (108) against the wall of the vertebra (100) by screwing the nut (119) along the anchoring means (101), in accordance with the first variant of implantation.

FIG. 17 also illustrates the positioning of the connector (208) against the wall of the vertebra (200) by sliding along the anchoring means (201), in accordance with the second variant of implantation.

FIG. 17 also illustrates the positioning of the connector (308) against the wall of the vertebra (300), in accordance with the third variant of implantation.

Figure 18:
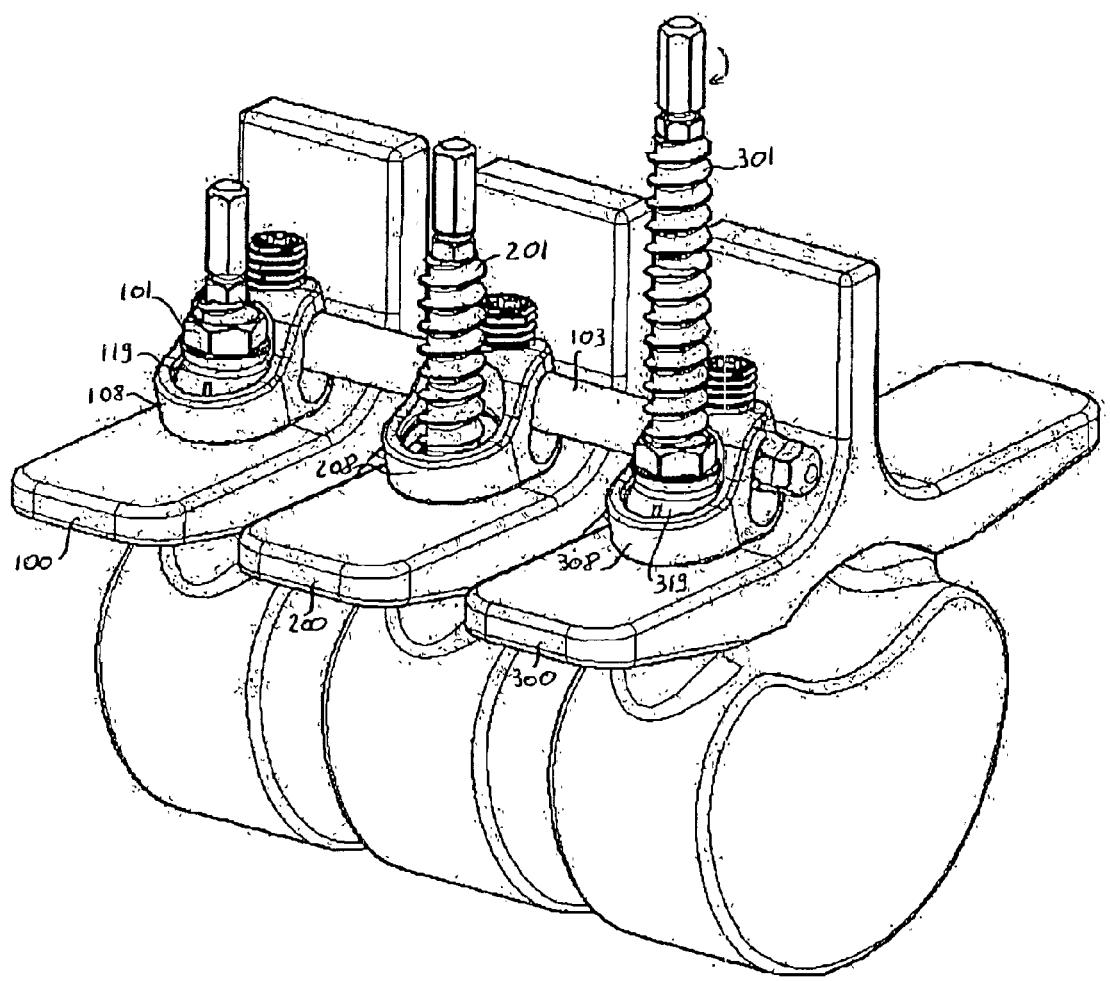

FIG. 18 illustrates the positioning of an anchoring means (301) in the vertebra (300) via the connection means (319), in accordance with the third variant of implantation.

Figure 19:
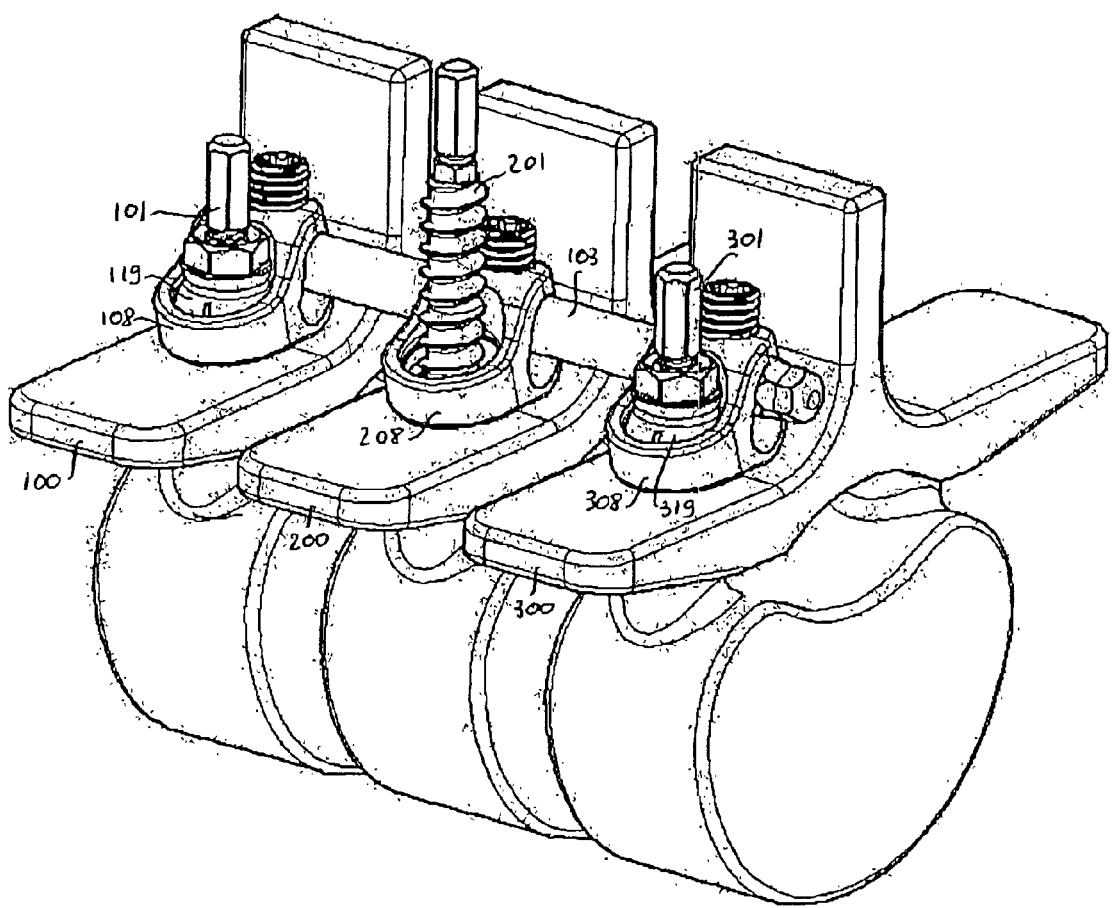

FIG. 19 illustrates the screwing of the anchoring means (301) into the vertebra (300) via the connection means (319), in accordance with the third variant of implantation.

Figure 20:
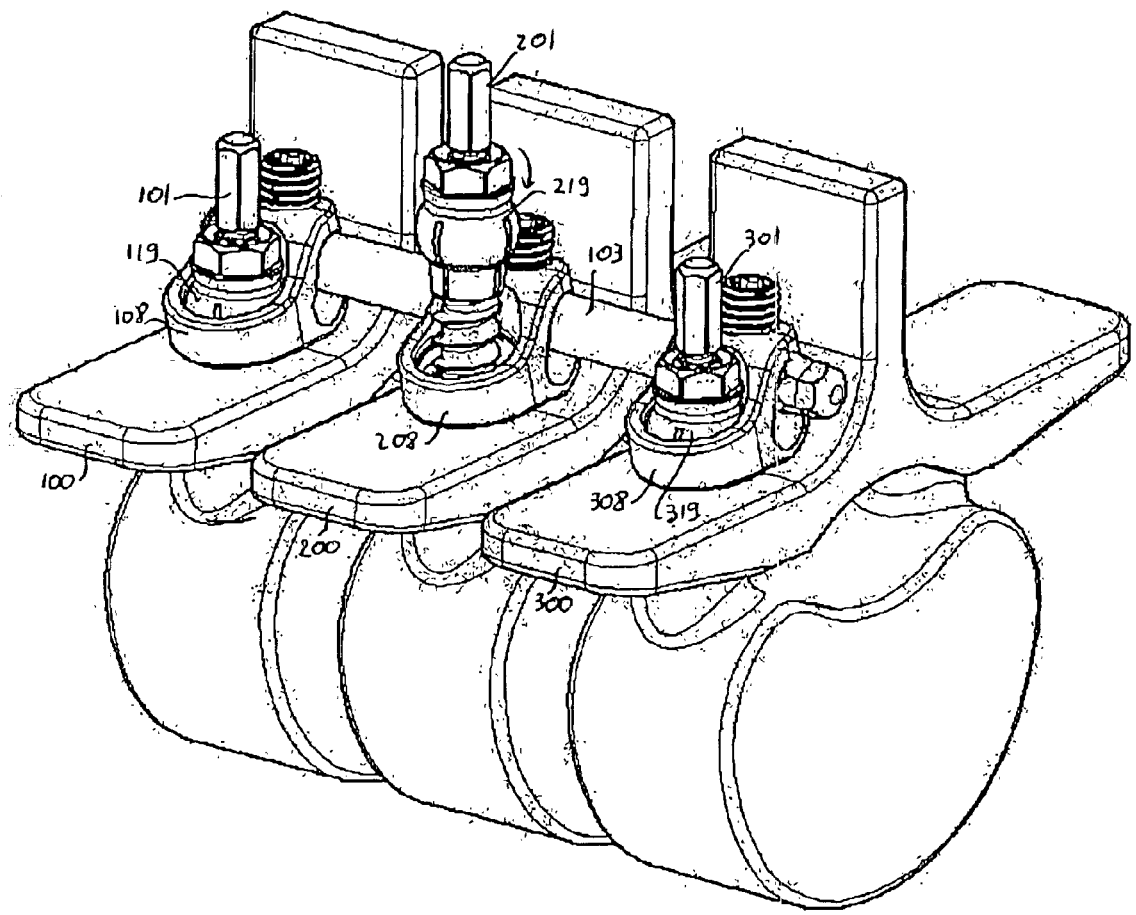

FIG. 20 illustrates the positioning of a connection means formed by a nut (219) by screwing it along the anchoring means (201), in accordance with the second variant of implantation.

Figure 21:
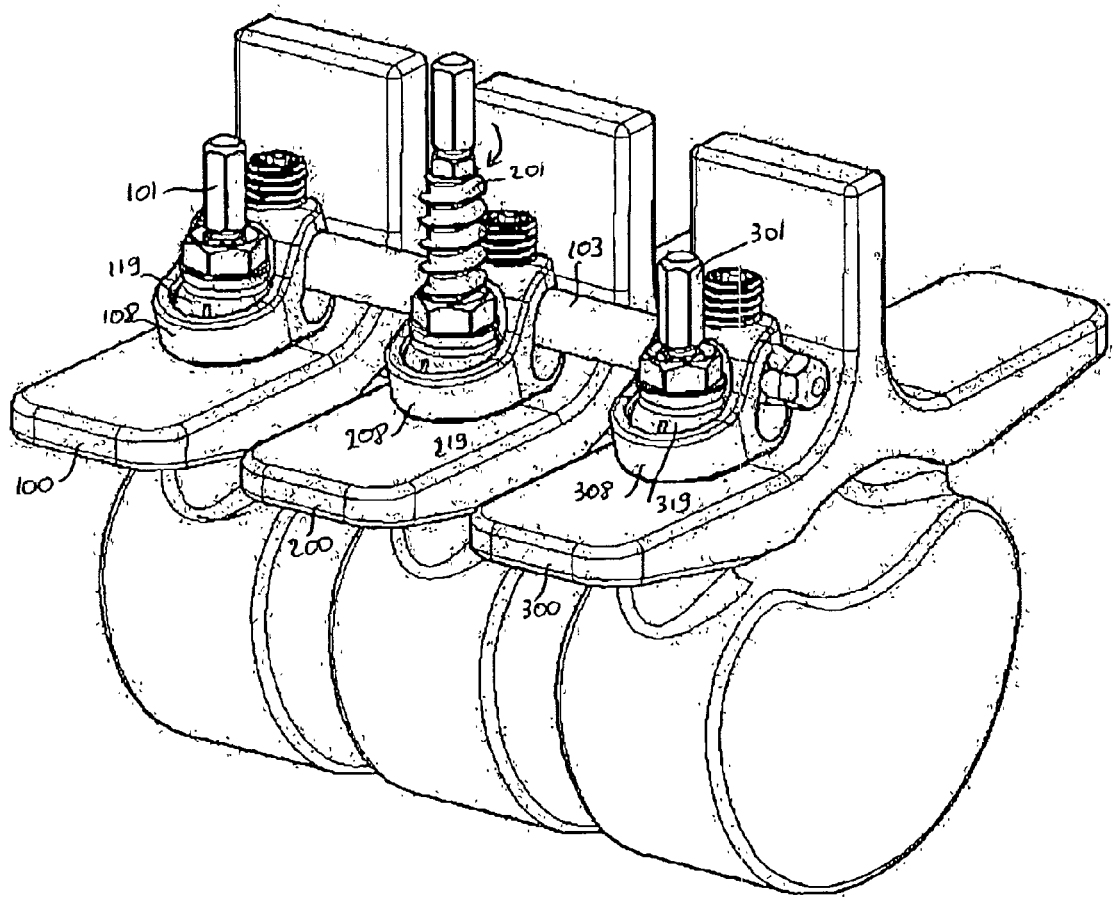

FIG. 21 illustrates the positioning of the nut (219) in the connector (208). Once in place, the anchoring means (201) can be screwed into the vertebra (200) via the connection means (219), in accordance with the third variant of implantation.

Figure 22:
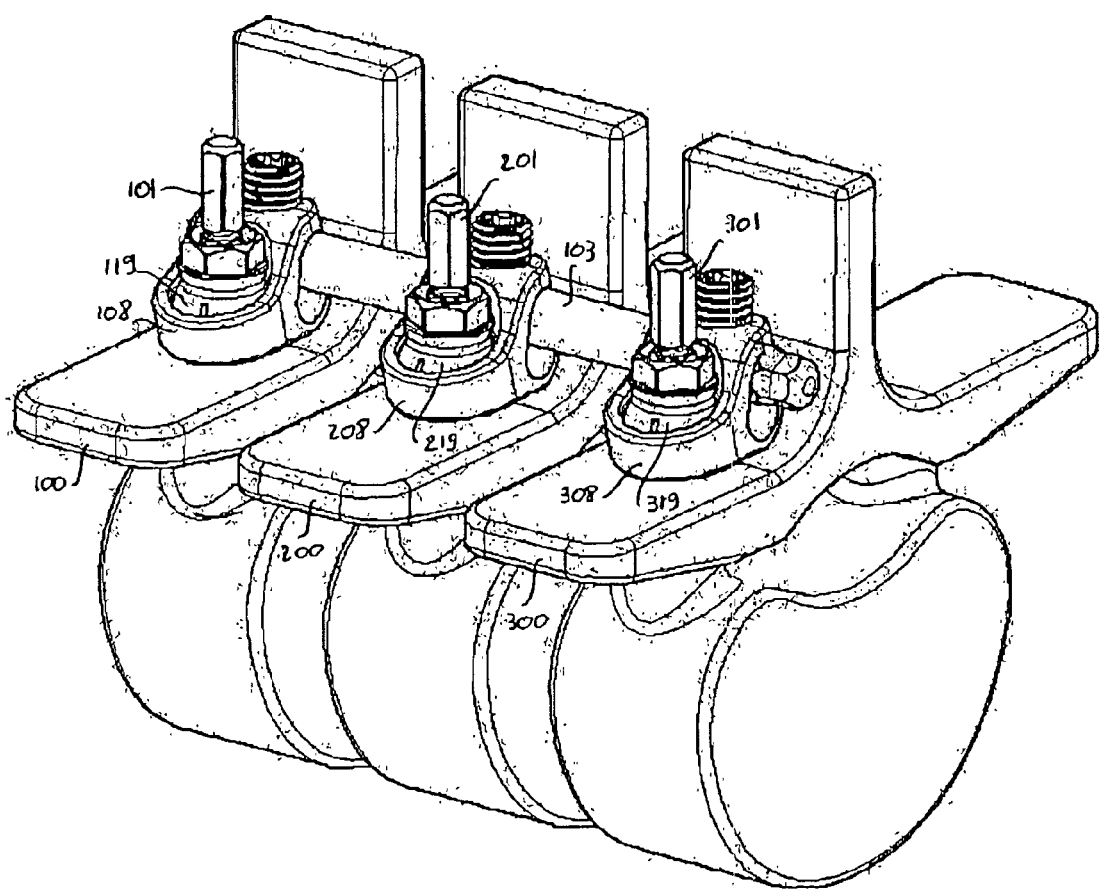

FIG. 22 illustrates each of the three variants of implantation when the implantation is completed.

However, at this stage it may happen that the surgeon notices that an anchoring means is poorly positioned. It may therefore be desirable to change the orientation of an anchoring means without removing the connection assembly and a fortiori the complete osteosynthesis system.

Figure 23:
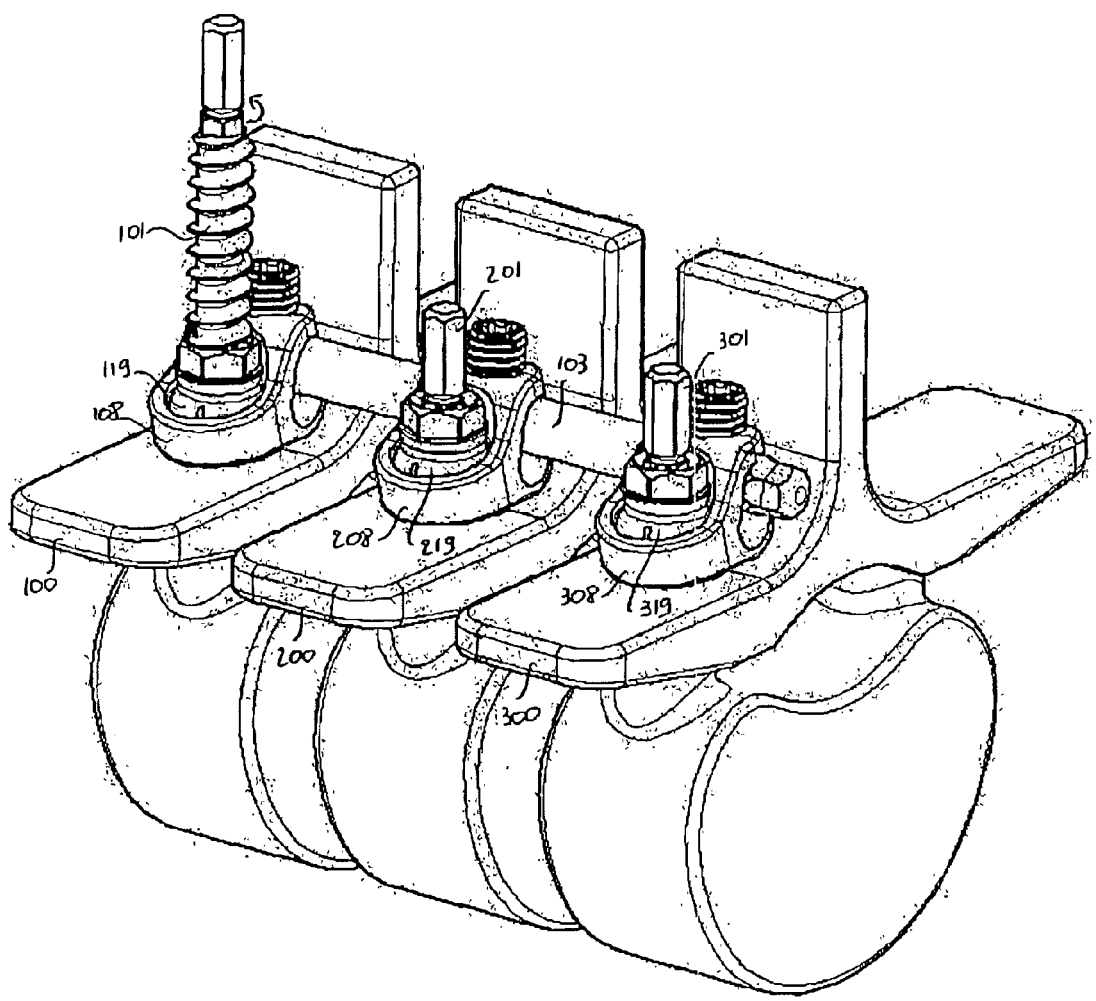

FIG. 23 illustrates the removal of the anchoring means (101) by unscrewing it relative to the nut (119). The nut (119), the connector (108) and the linking element (103) remain in place.

Figure 24:
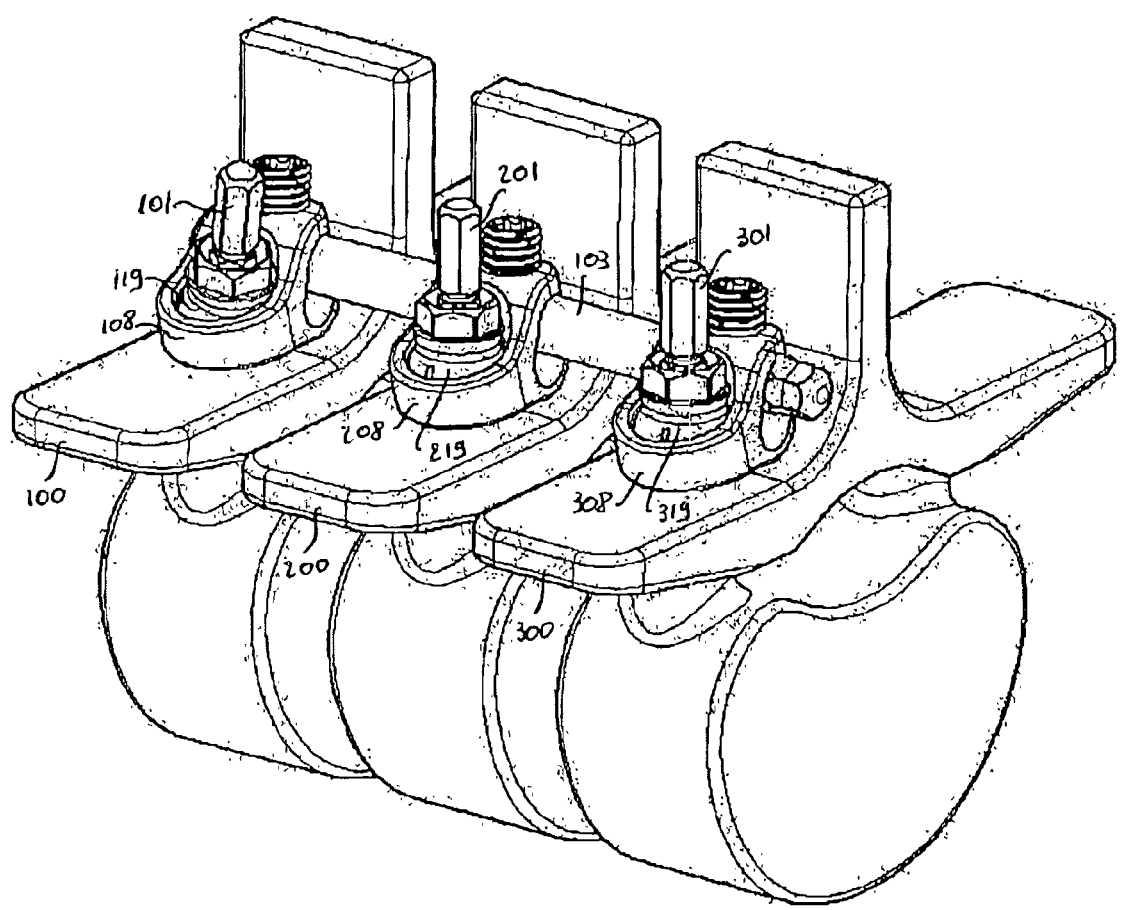
Figure 25:
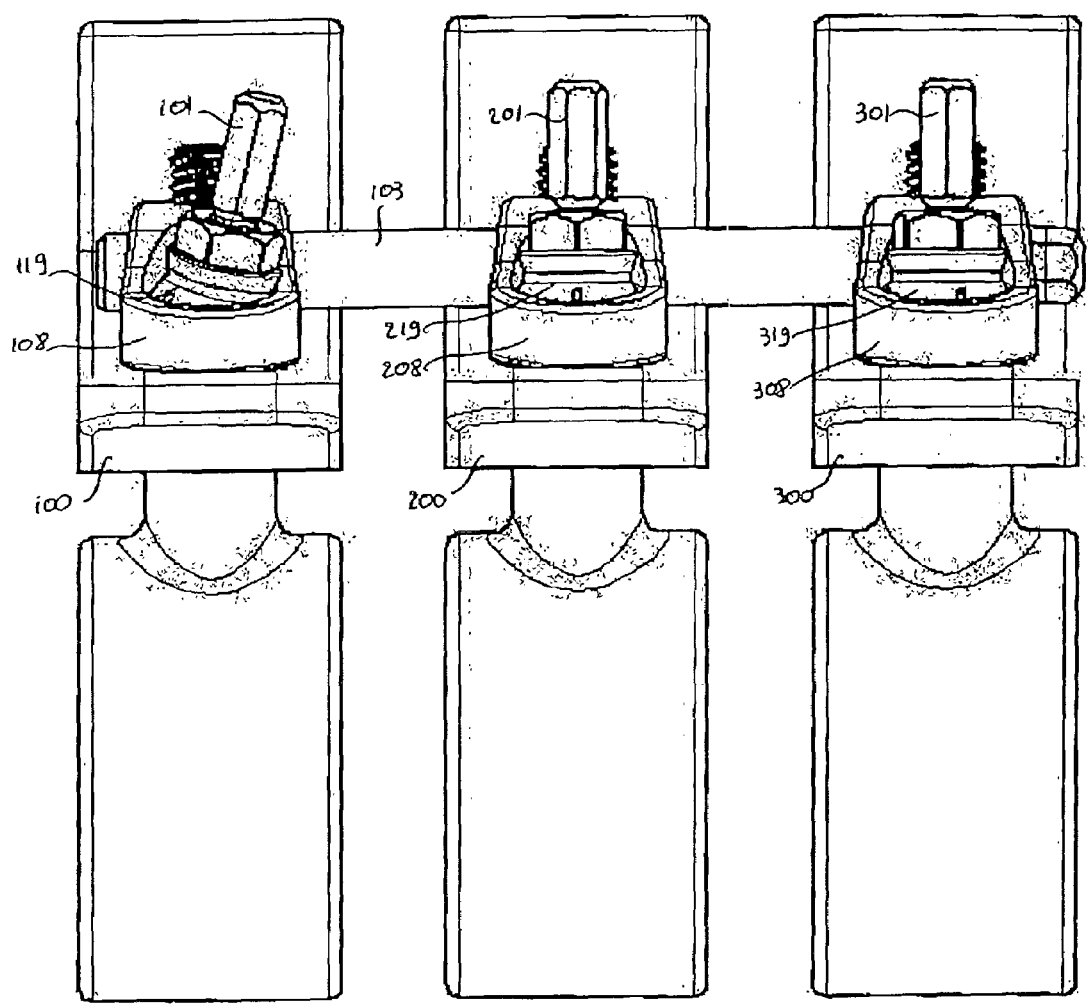

FIGS. 24 and 25 illustrate the repositioning of the anchoring means (101) in the vertebra (100) in a different orientation, by screwing the anchoring means (101) via the nut (119).

The invention claimed is:

1. A method for implementing at least one connection assembly for spinal osteosynthesis comprising a connector having a cavity forming a housing of a connecting means and at least one location for accommodating a linking element or a locking cylinder, said at least one location opening into the cavity forming the housing of said connecting means, and the connection means having, in its lower part, a spherical shape part in order to permit a free positioning of the connection means in the connector having a cavity of complementary shape to said spherical shape, said spherical shape part forming a limit of longitudinal positioning with the connector, the method comprising the steps of:
 connecting at least one linking element to a bone-anchoring means with the aid of said connection assembly,
 said connecting step comprising using said bone-anchoring means comprising a connection zone intended to cooperate with said connection means,
 ensuring the fixation of said bone-anchoring means relative to the connector via the connection means; and
 blocking the connection assembly connected by pressure of the linking element or the locking cylinder on the spherical shape of said connection means the method further comprises the steps of pre-fitting the connection means in said connector; placing the bone-anchoring means in the bone; and introducing the connection means along the anchoring means.

2. The method for implementing at least one connection assembly for spinal osteosynthesis as claimed in claim 1, further comprising engaging the linking element in the connector before the introduction of the connector on the anchoring means.

3. The method for implementing at least one connection assembly for spinal osteosynthesis as claimed in claim 1, further comprising ensuring the alignment of the connection means during its positioning by a preliminary guiding part situated on the bone-anchoring means.

4. The method for implementing at least one connection assembly for spinal osteosynthesis as claimed in claim 1, further comprising blocking the linking element relative to said connector by screwing a blocking nut into a blocking site which opens out into a site receiving the linking element.

5. A method for implementing at least one connection assembly for spinal osteosynthesis comprising a connector having a cavity forming a housing of a connecting means and at least one location for accommodating a linking element or a locking cylinder, said at least one location opening into the cavity forming the housing of said connecting means, and the connection means having, in its lower part, a spherical shape part in order to permit a free positioning of the connection means in the connector having a cavity of complementary shape to said spherical shape, said spherical shape part forming a limit of longitudinal positioning with the connector, the method comprising the steps of:
 connecting at least one linking element to a bone-anchoring means with the aid of said connection assembly,
 said connecting step comprising using said bone-anchoring means comprising a connection zone intended to cooperate with said connection means,
 ensuring the fixation of said bone-anchoring means relative to the connector via the connection means;
 blocking the connection assembly connected by pressure of the linking element or the locking cylinder on the spherical shape of said connection means;
 pre-fitting the connection means in said connector;
 placing the bone-anchoring means in the bone;
 introducing the connection means along the anchoring means engaging the linking element in the connector after the introduction of the connector on the anchoring means; and
 engaging the linking element in the connector after the introduction of the connector on the anchoring means.

6. A method for implementing at least one connection assembly for spinal osteosynthesis comprising a connector having a cavity forming a housing of a connecting means and at least one location for accommodating a linking element or a locking cylinder, said at least one location opening into the cavity forming the housing of said connecting means, and the connection means having, in its lower part, a spherical shape part in order to permit a free positioning of the connection means in the connector having a cavity of complementary shape to said spherical shape, said spherical shape part forming a limit of longitudinal positioning with the connector, the method comprising the steps of:
 connecting at least one linking element to a bone-anchoring means with the aid of said connection assembly,
 said connecting step comprising using said bone-anchoring means comprising a connection zone intended to cooperate with said connection means,
 ensuring the fixation of said bone-anchoring means relative to the connector via the connection means;

blocking the connection assembly connected by pressure of the linking element or the locking cylinder on the spherical shape of said connection means; and further comprising, in succession, first placing the bone-anchoring means in the bone, introducing the connector, equipped with the linking element, along the anchoring means, and finally introducing the connection means along the anchoring means.

7. A method for implementing at least one connection assembly for spinal osteosynthesis comprising a connector having a cavity forming a housing of a connecting means and at least one location for accommodating a linking element or a locking cylinder, said at least one location opening into the cavity forming the housing of said connecting means, and the connection means having, in its lower part, a spherical shape part in order to permit a free positioning of the connection means in the connector having a cavity of complementary shape to said spherical shape, said spherical shape part forming a limit of longitudinal positioning with the connector, the method comprising the steps of:

connecting at least one linking element to a bone-anchoring means with the aid of said connection assembly, said connecting step comprising using said bone-anchoring means comprising a connection zone intended to cooperate with said connection means, ensuring the fixation of said bone-anchoring means relative to the connector via the connection means; and blocking the connection assembly connected by pressure of the linking element or the locking cylinder on the spherical shape of said connection means; the method further comprises the steps of, before implantation in the bone, pre-fitting the connection assembly without the anchoring means, and introducing the anchoring means into the bone via said connection means, when said connection assembly is correctly positioned against the bone.

8. The method for implementing at least one connection assembly for spinal osteosynthesis as claimed in claim 7, further comprising choosing the orientation of the connection means as a function of the desired orientation of the bone-anchoring means.

9. The A method for implementing at least one connection assembly for spinal osteosynthesis comprising a connector having a cavity forming a housing of a connecting means and at least one location for accommodating a linking element or a locking cylinder, said at least one location opening into the cavity forming the housing of said connecting means, and the connection means having, in its lower part, a spherical shape part in order to permit a free positioning of the connection means in the connector having a cavity of complementary shape to said spherical shape, said spherical shape part forming a limit of longitudinal positioning with the connector, the method comprising the steps of:

connecting at least one linking element to a bone-anchoring means with the aid of said connection assembly, said connecting step comprising using said bone-anchoring means comprising a connection zone intended to cooperate with said connection means, ensuring the fixation of said bone-anchoring means relative to the connector via the connection means;

blocking the connection assembly connected by pressure of the linking element or the locking cylinder on the spherical shape of said connection means; and further comprising blocking the linking element relative to said connector by introducing a blocking cylinder into a blocking site which opens out on the one hand into the cavity forming the seat of the spherical part and on the other hand into a site receiving the linking element, and by blocking said blocking cylinder with the aid of a blocking nut.

10. The A method for implementing at least one connection assembly for spinal osteosynthesis comprising a connector having a cavity forming a housing of a connecting means and at least one location for accommodating a linking element or a locking cylinder, said at least one location opening into the cavity forming the housing of said connecting means, and the connection means having, in its lower part, a spherical shape part in order to permit a free positioning of the connection means in the connector having a cavity of complementary shape to said spherical shape, said spherical shape part forming a limit of longitudinal positioning with the connector, the method comprising the steps of:

connecting at least one linking element to a bone-anchoring means with the aid of said connection assembly, said connecting step comprising using said bone-anchoring means comprising a connection zone intended to cooperate with said connection means, ensuring the fixation of said bone-anchoring means relative to the connector via the connection means;

blocking the connection assembly connected by pressure of the linking element or the locking cylinder on the spherical shape of said connection means; and wherein said linking element comprises a first linking element and said method further comprising blocking the first linking element relative to said connector by introducing another linking element into a blocking site which opens out on the one hand into the cavity forming the seat of the spherical part and on the other hand into a site receiving the first linking element, and by blocking said second linking element with the aid of a blocking nut.

11. A method for implementing at least one connection assembly for spinal osteosynthesis comprising a connector having a cavity forming a housing of a connecting means and at least one location for accommodating a linking element or a locking cylinder, said at least one location opening into the cavity forming the housing of said connecting means, and the connection means having, in its lower part, a spherical shape part in order to permit a free positioning of the connection means in the connector having a cavity of complementary shape to said spherical shape, said spherical shape part forming a limit of longitudinal positioning with the connector, the method comprising the steps of:

connecting at least one linking element to a bone-anchoring means with the aid of said connection assembly, said connecting step comprising using said bone-anchoring means comprising a connection zone intended to cooperate with said connection means, ensuring the fixation of said bone-anchoring means relative to the connector via the connection means; and blocking the connection assembly connected by pressure of the linking element or the locking cylinder on the spherical shape of said connection means; and further comprising providing slots machined in the spherical shape part of the connection means and deforming the slots machined in the spherical shape part of the connection means upon final tightening of said connection assembly.

12. A method for implementing at least one connection assembly for spinal osteosynthesis comprising the steps of:

connecting at least one linking element to a bone anchoring means with the aid of said connection assembly;

said connecting step comprising using bone-anchoring means comprising a connection zone intended to cooperate with a connection means having, in its lower part, a spherical shape part in order to permit a free positioning of the connection means in a connector having a cavity of complementary shape to said spherical shape, said spherical shape part forming a limit of longitudinal positioning with the connector;

ensuring the fixation of said bone-anchoring means relative to the connector via the connection means;

blocking the connection assembly by pressure of the at least one linking element or a locking cylinder on a spherical shape of said connection means; and exerting a force to generate rupturing of the bone-anchoring means at the level of a rupture slot formed on said bone-anchoring means which corresponds to a force necessary to ensure final tightening of said connection assembly.

13. A method for implementing at least one connection assembly for spinal osteosynthesis further comprising:

connecting at least one linking element to a bone-anchoring means with the aid of said connection assembly, said connecting step comprising using a bone-anchoring means comprising a connection zone intended to cooperate with a connection means having, in its lower part, a spherical shape in order to permit a free positioning of the connection means in a connector having a cavity of complementary shape to said spherical shape, this spherical shape forming a limit of longitudinal positioning with the connector, and removing the bone-anchoring means after implantation of said connector without modification of the positioning of said connector.

14. The method for implementing at least one connection assembly for spinal osteosynthesis as claimed in claim 13, further comprising changing the bone-anchoring means after implantation of said connector without modification of the positioning of said connector.

15. The method for implementing at least one connection assembly for spinal osteosynthesis as claimed in claim 13, further comprising repositioning the bone-anchoring means after implantation of said connector without modification of the positioning of said connector.

* * * * *

UNITED STATES PATENT AND TRADEMARK OFFICE
CERTIFICATE OF CORRECTION

PATENT NO. : 7,651,516 B2　　　　　　　　　　　　　　　　　　　　　Page 1 of 1
APPLICATION NO. : 10/282278
DATED : January 26, 2010
INVENTOR(S) : Petit et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1533 days.

Signed and Sealed this

Twenty-eighth Day of December, 2010

David J. Kappos
*Director of the United States Patent and Trademark Office*